United States Patent
Kanada

(10) Patent No.: US 12,039,717 B2
(45) Date of Patent: Jul. 16, 2024

(54) REGION DIVIDING DEVICE, METHOD, AND PROGRAM, SIMILARITY DETERMINING APPARATUS, METHOD, AND PROGRAM, AND FEATURE QUANTITY DERIVING APPARATUS, METHOD, AND PROGRAM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 427 days.

(21) Appl. No.: 17/183,369

(22) Filed: Feb. 24, 2021

(65) Prior Publication Data

US 2021/0183061 A1 Jun. 17, 2021

Related U.S. Application Data

(63) Continuation of application No. PCT/JP2019/028299, filed on Jul. 18, 2019.

(30) Foreign Application Priority Data

Aug. 31, 2018 (JP) .................................. 2018-162862

(51) Int. Cl.
*G06K 9/00* (2022.01)
*A61B 5/00* (2006.01)
(Continued)

(52) U.S. Cl.
CPC .............. *G06T 7/0012* (2013.01); *A61B 5/08* (2013.01); *A61B 5/4887* (2013.01); *G06F 18/22* (2023.01);
(Continued)

(58) Field of Classification Search
CPC ....... G06T 7/0014; G06T 7/0016; G06T 7/10; G06T 7/11; G06T 7/162;
(Continued)

(56) References Cited

U.S. PATENT DOCUMENTS

| | | | |
|---|---|---|---|
| 7,206,462 B1 * | 4/2007 | Betke | G06T 7/0012 382/280 |
| 8,958,613 B2 | 2/2015 | Kondo et al. | |

(Continued)

FOREIGN PATENT DOCUMENTS

| | | |
|---|---|---|
| JP | 2000342558 | 12/2000 |
| JP | 2003070781 | 3/2003 |

(Continued)

OTHER PUBLICATIONS

"International Search Report (Form PCT/ISA/210) of PCT/JP2019/028299," mailed on Oct. 1, 2019, with English translation thereof, pp. 1-5.

(Continued)

*Primary Examiner* — Atiba O Fitzpatrick
(74) *Attorney, Agent, or Firm* — JCIPRNET

(57) ABSTRACT

A lung region can be appropriately divided with a region dividing device, method, and program for dividing a lung region included in a medical image. A bronchus extracting unit 30 of a region dividing unit 22 extracts a bronchus from a lung region included in a medical image acquired by imaging a subject including a lung. A first dividing unit 31 to a fourth dividing unit 34 identify a plurality of branch positions of the bronchus and divide, based on the branch positions, the lung region into a plurality of regions.

14 Claims, 16 Drawing Sheets

(51) Int. Cl.
  *A61B 5/08* (2006.01)
  *G06F 18/22* (2023.01)
  *G06F 18/241* (2023.01)
  *G06T 7/00* (2017.01)
  *G06V 10/25* (2022.01)

(52) U.S. Cl.
  CPC .......... *G06F 18/241* (2023.01); *G06T 7/0014* (2013.01); *G06V 10/25* (2022.01); *G06T 2207/30061* (2013.01); *G06T 2207/30096* (2013.01); *G06V 2201/031* (2022.01)

(58) Field of Classification Search
  CPC . G06T 2207/20112; G06T 2207/20021; G06T 2207/30061; G06T 2207/30064; G06T 2207/30096; G06T 2207/30032; G06F 18/22; G06F 16/532; G06F 16/583; G06F 16/5838; G06F 16/5854; G06F 16/5862; G06V 10/761; G06V 10/751; G06V 10/757; G06V 10/759; G06V 10/443; G06V 10/74; G06V 10/75; G06V 2201/032; G16H 30/00; G16H 30/20; G16H 30/40; G16H 70/00; G16H 70/20; G16H 70/60; Y10S 707/99933; Y10S 707/99931; Y10S 707/99936; G01N 33/4833; G01N 15/10; G01N 2015/1006; G01N 33/505; G01N 33/5026; G01N 2015/1081
  See application file for complete search history.

(56) References Cited

U.S. PATENT DOCUMENTS

| | | | |
|---|---|---|---|
| 9,142,029 B2 | 9/2015 | Inoue | |
| 10,930,396 B2 | 2/2021 | Kanada | |
| 2005/0207630 A1* | 9/2005 | Chan | G06T 7/0012 382/131 |
| 2009/0185731 A1* | 7/2009 | Ray | G06T 7/12 382/131 |
| 2011/0190626 A1* | 8/2011 | Mizuno | G06T 7/0012 600/425 |
| 2011/0237938 A1* | 9/2011 | Mizuno | G06T 7/187 600/425 |
| 2013/0156158 A1* | 6/2013 | Noji | G16H 50/30 378/62 |
| 2014/0079306 A1* | 3/2014 | Inoue | G06T 7/12 382/131 |
| 2015/0187118 A1* | 7/2015 | Masumoto | G06T 15/08 345/419 |
| 2018/0125443 A1* | 5/2018 | Takebe | G06V 10/755 |
| 2018/0158186 A1* | 6/2018 | Wang | G06T 7/11 |
| 2018/0185101 A1* | 7/2018 | Yamada | A61B 34/20 |
| 2018/0225884 A1* | 8/2018 | Yamada | G06T 7/149 |
| 2018/0240232 A1* | 8/2018 | Wang | G06T 7/11 |
| 2019/0139227 A1* | 5/2019 | Wang | G06T 7/136 |
| 2019/0197688 A1* | 6/2019 | Moriwaki | G06T 7/11 |
| 2023/0106440 A1* | 4/2023 | Golden | G06V 10/82 382/131 |

FOREIGN PATENT DOCUMENTS

| | | |
|---|---|---|
| JP | 2008200368 | 9/2008 |
| JP | 2011118543 | 6/2011 |
| JP | 2011212312 | 10/2011 |
| JP | 2014073355 | 4/2014 |
| JP | 2017012382 | 1/2017 |
| WO | 2013065090 | 5/2013 |
| WO | 2018116727 | 6/2018 |

OTHER PUBLICATIONS

"International Preliminary Report on Patentability (Form PCT/IPEA/409) of PCT/JP2019/028299," completed on Jul. 15, 2020, with English translation thereof, pp. 1-12.

Adrien Depeursinge et al., "Case-based lung image categorization and retrieval for interstitial lung diseases: clinical workflow", Int J Cars, vol. 7, Jun. 2011, pp. 97-110.

Joseph Jacob et al., "Evaluation of computer-based computer tomography stratification against outcome models in connective tissue disease-related interstitial lung disease: a patient outcome study", BMC Medicine, vol. 14, Nov. 2016, pp. 1-13.

Tae Iwasawa, "Quantitative evaluation of CT image of interstitial pneumonia by computer", Journal of Tomography, vol. 41, Issue 2, Aug. 2014, with English abstract, pp. 1-11.

Hiroaki Takebe et al., "Similar CT image retrieval method based on lesion natures and their three-dimensional distribution", IEICE Technical Report, vol. 117, Issue 106, Jul. 2017, with English abstract, pp. 57-62.

Office Action of Japan Counterpart Application, with English translation thereof, issued on Nov. 9, 2021, pp. 1-15.

Asakura et al., "a method for dividing a lesion region of a non-specific interstitial pneumonitis X-ray CT image", Journal of the Institute of Electronics, vol. 33, Issue 2, 2004, with English abstract, pp. 180-188.

* cited by examiner

FIG. 11

| FINDING TYPE | EVALUATION VALUE |
|---|---|
| INFILTRATIVE SHADOW | 2.9 |
| GROUND GLASS OPACITY | 7.6 |
| RETICULAR SHADOW | 8.5 (MAXIMUM) |
| BRONCHODILATION | 3.2 |
| . . . | . . . |
| . . . | . . . |
| NORMAL LUNG | -7.1 |
| LOW-ABSORPTION REGION (EMPHYSEMA) | -12.3 |

FIG. 13

| FINDING TYPE | VOLUME |
|---|---|
| GROUND GLASS OPACITY | 20540 |
| INFILTRATIVE SHADOW | 11210 |
| LOW-ABSORPTION REGION | 2890 |
| BRONCHODILATION | 4030 |
| RETICULAR SHADOW | 9680 |
| CYST | 1430 |
| NORMAL REGION | 157830 |

| CASE IMAGE | SIMILARITY |
|---|---|
| IMG0012.dcm | 0.87 |
| IMG0254.dcm | 0.77 |
| IMG0123.dcm | 0.54 |
| IMG0022.dcm | 0.52 |

FIG. 18

| FINDING TYPE | REGION PATTERN | | |
| --- | --- | --- | --- |
| | FIRST | SECOND | SIXTH |
| GROUND GLASS OPACITY | 0.7 | 0.3 | 0 |
| RETICULAR SHADOW | 0.7 | 0.3 | 0 |
| DOT SHADOW | 0.3 | 0.4 | 0.3 |
| NODULAR SHADOW | 0 | 0.5 | 0.5 |
| . . . | | | |

FIG. 19

| FINDING TYPE | REGION PATTERN | | |
| --- | --- | --- | --- |
| | FIRST | SECOND | SIXTH |
| GROUND GLASS OPACITY | 1.0 | 0 | 0 |
| RETICULAR SHADOW | 1.0 | 0 | 0 |
| DOT SHADOW | 0.7 | 0.3 | 0 |
| NODULAR SHADOW | 0.5 | 0.5 | 0 |
| . . . | | | |

FIG. 20

| FINDING TYPE | REGION PATTERN | | |
| --- | --- | --- | --- |
| | FIRST | SECOND | SIXTH |
| GROUND GLASS OPACITY | 0 | 0.7 | 0.3 |
| RETICULAR SHADOW | 0 | 0.7 | 0.3 |
| DOT SHADOW | 0 | 0.3 | 0.7 |
| NODULAR SHADOW | 0 | 0 | 1.0 |
| . . . | | | |

REGION DIVIDING DEVICE, METHOD, AND PROGRAM, SIMILARITY DETERMINING APPARATUS, METHOD, AND PROGRAM, AND FEATURE QUANTITY DERIVING APPARATUS, METHOD, AND PROGRAM

CROSS-REFERENCE TO RELATED APPLICATIONS

This application is a Continuation of PCT International Application No. PCT/JP2019/028299 filed on Jul. 18, 2019, which claims priority under 35 U.S.C § 119(a) to Japanese Patent Application No. 2018-162862 filed on Aug. 31, 2018. Each of the above application(s) is hereby expressly incorporated by reference, in its entirety, into the present application.

BACKGROUND OF THE INVENTION

1. Field of the Invention

The present disclosure relates to a region dividing device, method, and a non-transitory computer readable recording medium storing a program for dividing a lung region included in a medical image, a similarity determining apparatus, method, and a non-transitory computer readable recording medium storing a program for determining a similarity between two medical images, and a feature quantity deriving apparatus, method, and program.

2. Description of the Related Art

In recent years, with advances of medical equipment such as a CT (Computed Tomography) apparatus and an MRI (Magnetic Resonance Imaging) apparatus, higher-quality high-resolution three-dimensional images have been increasingly used in image-based diagnosis.

On the other hand, in the medical fields, similar case search apparatuses are known which, based on an examination image such as a CT image to be examined, search for a past case that is similar to the examination image (see, for example, "Case-based lung image categorization and retrieval for interstitial lung diseases: clinical workflow", Adrien Depeursinge et al., Int J CARS (2012) 7:97-110, published online: 1 Jun. 2011, JPWO2013/65090A1, and JP2011-118543A). "Case-based lung image categorization and retrieval For interstitial lung diseases: clinical workflow", Adrien Depeursinge et al., Int J CARS (2012) 7:97-110, Published online: 1 Jun. 2011 has proposed a technique of classifying a lung case image into a plurality of regions respectively representing a plurality of types of tissues or lesions (hereinafter, tissues or lesions are collectively referred to as findings), registering the regions in a case database, similarly classifying a lung in an examination image into a plurality of regions respectively representing a plurality of finding types, and searching for a case image similar to the examination image based on the findings classification result of the examination image. In addition, JPWO2013/65090A1 and JP2011-118543A have proposed techniques of searching for an image similar to an examination image by comparing a feature quantity of an image, such as a density histogram, an average density, or a dispersion of the density of an image, with feature quantities of images registered in a database. In addition, as a technique of calculating a similarity between images, there has been proposed a technique of calculating a similarity for the entire region by setting a plurality of partial regions in at least one image among a plurality of images, determining, for each of the set partial regions, a similarity between the partial region and a corresponding region in another image, and performing weighted addition on the determined partial region similarities using respective weight coefficients set for the respective partial regions (see JP2000-342558A).

Interstitial pneumonia is known as a lung disease. Techniques of analyzing a CT image of a patient having interstitial pneumonia to classify and quantify a lesion representing particular findings such as a honeycomb lung, a reticular shadow, and a cyst included in the CT image have been proposed (see "Evaluation of computer-based computer tomography stratification against outcome models in connective tissue disease-related interstitial lung disease: a patient outcome study", Joseph Jacob et al., BMC Medicine (2016) 14:190, DOI 10.1186/s12916-016-0739-7 and "Quantitative evaluation of CT image of interstitial pneumonia by computer", Tae Iwasawa, Journal of Tomography, Vol. 41, No. 2, August 2014). By analyzing a CT image and classifying and quantifying a lesion in this manner, the degree of the lung disease can be easily determined. In addition, by assigning different colors to the regions classified and quantified in such a manner and displaying the regions, how much region of a specific symptom is included in the image can be easily diagnosed.

When a diagnosis is made using a lung image as described above, it is diagnostically important to divide the lung region into anatomical lung sections (an upper lobe, a middle lobe, and a lower lobe). Accordingly, a technique of extracting a bronchus or bronchi from a three-dimensional image including lungs, dividing a bronchial structure based on divergence of the bronchial structure, and dividing a lung region into lung sections based on the bronchial structure has been proposed (see JP2014-73355A). A technique of dividing a lung region into a plurality of regions at predetermination percentages based on a distance from a surface of a lung has also been proposed (see JP2017-12382A).

SUMMARY OF THE INVENTION

However, in a case of an advanced disease, the borders of the lung sections become unclear or the deformation of the bronchi on the peripheral side becomes large. Therefore, even if the bronchial structure is used as described in JP2014-73355A, it is difficult to perform region division based on the lung sections. In such a circumstance, when a lung region is divided into a plurality of regions at predetermined percentages based on a distance from a surface of a lung as described in JP2017-12382A, a change in region size due to expansion or contraction of a diseased region is distributed to the divided regions. Thus, the diseased region can no longer be recognized as a feature of the region.

The present invention is made in view of the circumstance described above and aims to enable a lung region included in an image to be appropriately divided.

A region dividing device according to the present disclosure includes a bronchus extracting unit that extracts a bronchus from a lung region included in a medical image acquired by imaging a subject including a lung; and a dividing unit that identifies a plurality of branch positions of the bronchus and divides, based on the branch positions, the lung region into a plurality of regions.

In the region dividing device according to the present disclosure, the dividing unit may include a first dividing unit that divides, based on the branch positions, the lung region into a plurality of regions in an up-down direction.

The term "up-down direction" refers to a body axis direction of a patient who is the subject for whom the medical image is acquired.

In the region dividing device according to the present disclosure, the first dividing unit may divide the lung region into three regions with reference to a first bronchi branch and a third bronchi branch among the plurality of branch positions, the three regions being an upper region, a middle region, and a lower region. The first bronchi branch in the present disclosure is equivalent to a branch of the trachea and the left and right bronchi. In the present disclosure, the branches that appear from the first bronchi branch toward the bronchial periphery are sequentially referred to as a second bronchi branch, a third bronchi branch, and so on.

In the region dividing device according to the present disclosure, the dividing unit may include a second dividing unit that divides the lung region into a region that is within a specific distance from a specific branch position among the plurality of branch positions and a region other than the region that is within the specific distance.

In the region dividing device according to the present disclosure, the second dividing unit may set a third bronchi branch as the specific branch position among the plurality of branch positions, and may divide the lung region into a central region that is within the specific distance from the third bronchi branch and a region other than the central region.

In the region dividing device according to the present disclosure, the dividing unit may include a third dividing unit that further divides the lung region into an outer region and an inner region.

In the region dividing device according to the present disclosure, the dividing unit may include a fourth dividing unit that further divides the lung region into a dorsal region and a ventral region.

A similarity determining apparatus according to the present disclosure is a similarity determining apparatus that determines a similarity between a first medical image including a lung and a second medical image including a lung and that includes
  the region dividing device, according to the present disclosure, that divides a lung region in the first medical image into a plurality of regions;
  a findings classifying unit that classifies each of pixels of the first medical image into at least one of findings;
  a feature quantity calculating unit that calculates, for each of the divided regions, first feature quantities for respective findings classified in the first medical image;
  a region similarity deriving unit that derives, for each of the divided regions, a region similarity between the first medical image and the second medical image, based on the first feature quantities for the respective findings calculated in the first medical image and second feature quantities for the respective findings calculated in advance in the second medical image; and
  a similarity deriving unit that derives a similarity between the first medical image and the second medical image, based on the plurality of region similarities.

A feature quantity deriving apparatus according to the present disclosure includes the region dividing device, according to the present disclosure, that divides a lung region in a medical image into a plurality of regions,
  a findings classifying unit that classifies each of pixels of the medical image into at least one of findings, and
  a feature quantity calculating unit that calculates, for each of the divided regions, feature quantities for respective findings classified in the medical image.

The feature quantity deriving device according to the present disclosure may further include a display control unit that displays the feature quantity on a display unit.

A region dividing method according to the present disclosure includes extracting a bronchus from a lung region included in a medical image acquired by imaging a subject including a lung; and
  identifying a plurality of branch positions of the bronchus and divides, based on the branch positions, the lung region into a plurality of regions.

A similarity determining method according to the present disclosure is a similarity determining method for determining a similarity between a first medical image including a lung and a second medical image including a lung, the similarity determining method including:
  dividing a lung region in the first medical image into a plurality of regions in accordance with the region dividing method according to the present disclosure;
  classifying each of pixels of the first medical image into at least one of findings;
  calculating, for each of the divided regions, first feature quantities for respective findings classified in the first medical image;
  deriving, for each of the divided regions, a region similarity between the first medical image and the second medical image, based on the first feature quantities for the respective findings calculated in the first medical image and second feature quantities for the respective findings calculated in advance in the second medical image; and
  deriving a similarity between the first medical image and the second medical image, based on the plurality of region similarities.

A feature quantity deriving method according to the present disclosure includes dividing a lung region in a medical image into a plurality of regions;
  classifying each of pixels of the medical image into at least one of findings; and
  calculating, for each of the divided regions, feature quantities for respective findings classified in the first medical image.

The region dividing method, the similarity determining method, and the feature quantity deriving method according to the present disclosure may be provided as a non-transitory computer readable recording medium storing a program for causing a computer to execute the methods.

Another region dividing device according to the present disclosure includes a memory that stores instructions to be executed by a computer, and
  a processor configured to execute the stored instructions, wherein the processor executes a process of
  extracting a bronchus from a lung region included in a medical image acquired by imaging a subject including a lung, and
  identifying a plurality of branch positions of the bronchus and divides, based on the branch positions, the lung region into a plurality of regions.

Another similarity determining apparatus according to the present disclosure includes a memory that stores instructions for causing a computer to execute a process of determining a similarity between a first medical image and a second medical image, and
  a processor configured to execute the stored instructions, wherein the processor executes a process of
  dividing a lung region in the first medical image into a plurality of regions in accordance with the region dividing method according to the present disclosure, classifying each of pixels of the first medical image into at least one of findings, calculating, for each of the divided regions, first feature quantities for respective findings classified in the first medical image, deriving, for each of the divided regions, a region similarity between the first medical image and the second medical image, based on the first feature quantities for the respective findings calculated in the first medical image and second feature quantities for the respective findings calculated in advance in the second medical image, and deriving a similarity between the first medical image and the second medical image, based on the plurality of region similarities.

Another feature quantity deriving apparatus according to the present disclosure includes a memory that stores instructions to be executed by a computer, and a processor configured to execute the stored instructions, wherein the processor executes a process of dividing a lung region in a medical image into a plurality of regions in accordance with the region dividing method according to the present disclosure, classifying each of pixels of the medical image into at least one of findings; and calculating, for each of the divided regions, feature quantities for respective findings classified in the first medical image.

The region dividing device, method, and non-transitory computer readable recording medium storing program according to the present disclosure enable a lung region to be divided based on branch positions of the bronchi independently from the lung sections and independently from the predetermined percentages. Therefore, the lung region can be appropriately divided.

The similarity determining apparatus, method, and program according to the present disclosure enable a similarity between a first medical image and a second medical image to be appropriately determined by appropriately performing weighting according to the positions and distributions of findings in a target region.

BRIEF DESCRIPTION OF THE DRAWINGS

FIG. 11 is a diagram illustrating evaluation values corresponding to respective finding types for a center pixel of a certain region of interest;

FIG. 13 is a diagram illustrating calculation results of volumes of findings;

FIG. 14 is a diagram illustrating a search result list;

FIG. 18 is a diagram illustrating weight coefficients corresponding to respective region patterns;

FIG. 19 is a diagram illustrating weight coefficients corresponding to respective region patterns; and FIG. 20 is a diagram illustrating weight coefficients corresponding to respective region patterns.

DESCRIPTION OF THE PREFERRED EMBODIMENTS

Figure 1:
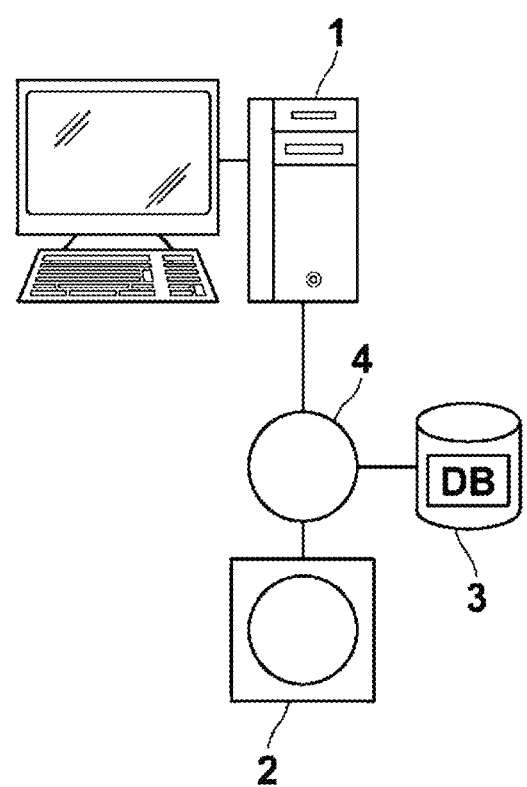
FIG. 1 is a hardware configuration diagram illustrating an overview of a diagnosis support system to which a similarity determining apparatus including a region dividing device according to a first embodiment of the present disclosure is applied.

Embodiments of the present disclosure will be described below with reference to the drawings. FIG. 1 is a hardware configuration diagram illustrating an overview of a diagnosis support system to which a similarity determining apparatus including a region dividing device according to a first embodiment of the present disclosure is applied. As illustrated in FIG. 1, in the diagnosis support system, a similarity determining apparatus 1 including a region dividing device according to the present embodiment, a three-dimensional imaging apparatus 2, and an image storage server 3 are connected via a network 4 to be able to communicate with each other.

The three-dimensional imaging apparatus 2 is an apparatus that images a site serving as a diagnosis target of a subject to generate a three-dimensional image representing the site, and specifically is a CT apparatus, an MRI apparatus, a PET (Positron Emission Tomography) apparatus, and the like. The three-dimensional image constituted by a plurality of slice images generated by this three-dimensional imaging apparatus 2 is transmitted to and stored in the image storage server 3. In the present embodiment, the diagnosis-target site of a patient who is a subject is lungs, and the three-dimensional imaging apparatus 2 is a CT apparatus and generates, as a three-dimensional image, a CT image of the chest including the lungs of the subject.

The image storage server 3 is a computer that stores and manages various kinds of data, and includes a mass external storage device and database management software. The image storage server 3 communicates with the other apparatuses via the wired or wireless network 4 to transmit and receive image data or the like. Specifically, the image storage server 3 acquires, via the network 4, various kinds of data including image data of a three-dimensional image generated by the three-dimensional imaging apparatus 2, and stores and manages the various kinds of data on a recording medium such as the mass external storage device. The storage format of the image data and communication performed between the apparatuses via the network 4 are based on a protocol such as DICOM (Digital Imaging and Communication in Medicine). It is assumed that in the present embodiment, the image storage server 3 stores a three-dimensional image to be examined (hereinafter, referred to as an examination image) and a case database DB in which case images are registered. The case database DB will be described later. In the present embodiment, an examination image is a three-dimensional image constituted by one or more slice images (hereinafter, referred to as examination slice images). A case image is also a three-dimensional image constituted by one or more slice images (hereinafter, referred to as case slice images). The examination image corresponds to a first medical image, and the case image corresponds to a second medical image.

The similarity determining apparatus 1 is a single computer on which a similarity determining program including a region dividing program according to the present disclosure is installed. The computer may be a workstation or a personal computer directly operated by a doctor who makes a diagnosis, or may be a server computer connected to the workstation or the personal computer via a network. The similarity determining program is recorded on a recording medium such as a DVD (Digital Versatile Disc) or a CD-ROM (Compact Disc Read Only Memory), is distributed, and is installed on the computer from the recording medium. Alternatively, the similarity determining program is stored in a storage device of a server computer connected to the network or in a network storage in an externally accessible state and is downloaded to and installed on a computer used by a doctor in response to a request.

Figure 2:
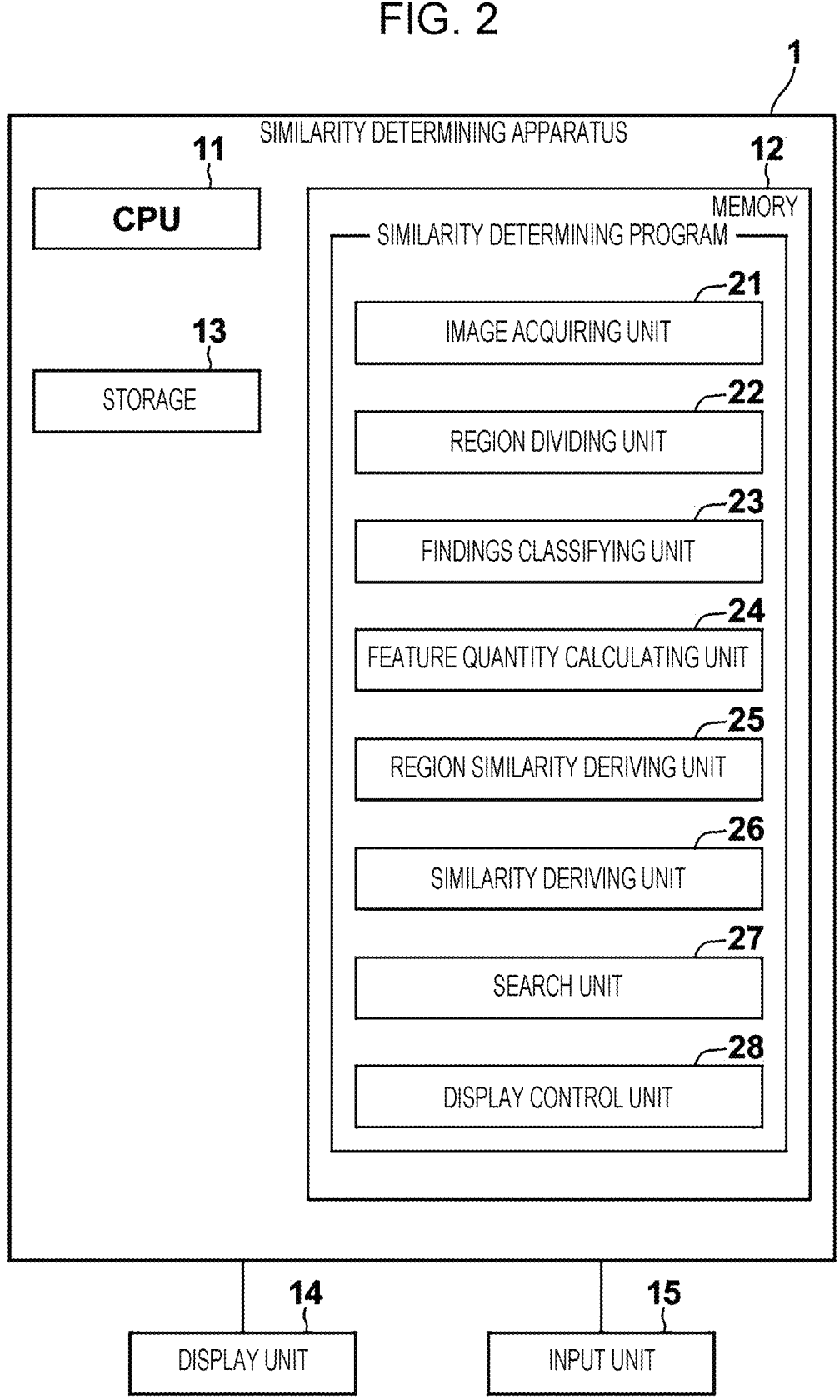
FIG. 2 is a schematic block diagram illustrating a configuration of the similarity determining apparatus including the region dividing device according to the first embodiment.

FIG. 2 is a diagram illustrating a schematic configuration of the similarity determining apparatus according to an embodiment of the present disclosure, which is implemented by installing the similarity determining program on a computer. As illustrated in FIG. 2, the similarity determining apparatus 1 includes a CPU (Central Processing Unit) 11, a memory 12, and a storage 13 as a configuration of a standard workstation. A display unit 14 constituted by a liquid crystal display or the like and an input unit 15 constituted by a keyboard and mouse or the like are connected to the similarity determining apparatus 1.

The storage 13 is constituted by a hard disk, an SSD (Solid State Drive), and the like. The storage 13 stores various kinds of information including an examination image of a subject and information necessary for processing, which are acquired from the image storage server 3 via the network 4.

The memory 12 stores the similarity determining program. The similarity determining program defines, as processes which the similarity determining program causes the CPU 11 to execute, an image acquisition process of acquiring an examination image to be examined; a region division process according to the present disclosure of dividing a target region in the examination image into a plurality of regions; a findings classification process of classifying each of pixels of the examination image into at least one of findings; a feature quantity calculation process of calculating, for each of the divided regions, first feature quantities for respective findings classified in the examination image; a region similarity derivation process of deriving, for each of the divided regions, a region similarity between of the examination image and the case image, based on the first feature quantities calculated for the respective findings in the examination image and second feature quantities calculated in advance for the respective findings in a case image; a similarity derivation process of deriving a similarity between the examination image and the case image by performing a weighted calculation on the plurality of region similarities using weight coefficients based on at least one of sizes of the respective divided regions or sizes of a specific finding included in the respective divided regions; a search process of searching for, based on the derived similarity, a case image similar to the examination image; and a display control process of displaying a search result on the display unit 14.

Figure 3:
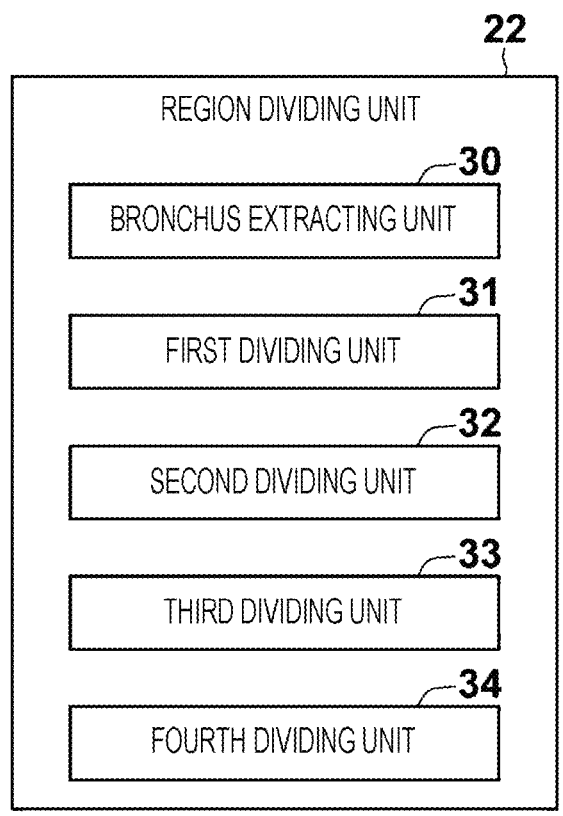
FIG. 3 is a schematic block diagram illustrating a configuration of a region dividing unit.

The CPU 11 performs these processes in accordance with the program. Consequently, the computer functions as an image acquiring unit 21, a region dividing unit 22, a findings classifying unit 23, a feature quantity calculating unit 24, a region similarity deriving unit 25, a similarity deriving unit 26, a search unit 27, and a display control unit 28. The region dividing unit 22 corresponds to a region dividing device according to the present disclosure. FIG. 3 is a schematic block diagram illustrating a configuration of the region dividing unit 22. The configuration of the region dividing unit 22 will be described later.

The memory 12 also stores a region dividing program for performing the region division process. The region dividing program defines, as the region division process which the region division program causes the CPU 11 to execute, a bronchus extraction process of extracting a bronchus from a lung region included in an examination image, a first division process of dividing, based on branch positions of the bronchus, the lung region into a plurality of regions in an up-down direction, a second division process of dividing the lung region into a region that is within a specific distance from a specific branch position among a plurality of branch positions and a region other than the region that is within the specific distance, a third division process of dividing the lung region into an outer region and an inner region, and a fourth division process of dividing the lung region into a dorsal region and a ventral region.

The CPU 11 performs these processes in accordance with the program. Consequently, the computer functions as a bronchus extracting unit 30, a first dividing unit 31, a second dividing unit 32, a third dividing unit 33, and a fourth dividing unit 34 that constitute the region dividing unit 22 as illustrated in FIG. 3. Note that the first dividing unit 31, the second dividing unit 32, the third dividing unit 33, and the fourth dividing unit 34 correspond to a dividing unit according to the present disclosure.

The image acquiring unit 21 acquires an examination image V0 of a subject to be examined. When the examination image V0 is already stored in the storage 13, the image acquiring unit 21 may acquire the examination image V0 from the storage 13.

The region dividing unit 22 divides a lung region in an examination image into a plurality of regions. The region division process will be described in detail below. As illustrated in FIG. 3, the region dividing unit 22 has the bronchus extracting unit 30 that extracts a bronchial region from a lung region in an examination image; the first dividing unit 31 that divides, based on branch positions of the bronchus, the lung region into a plurality of regions in an up-down direction; the second dividing unit 32 that divides the lung region into a region that is within a specific distance from a specific branch position among a plurality of branch positions and a region other than the region that is within the specific distance; the third dividing unit 33 that divides the lung region into an outer region and an inner region; and the fourth dividing unit 34 that divides the lung region into a dorsal region and a ventral region.

The bronchus extracting unit 30 extracts, as a bronchial region, a bronchial structure from the examination image V0. For this purpose, the bronchus extracting unit 30 extracts a lung region, which is a target region, from the examination image V0. As a technique of extracting a lung region, any technique such as a method of representing signal values of respective pixels in the examination image V0 as a histogram and performing a threshold-based processing on the lung to extract the lung region or a region expansion technique (region growing) based on a seed point representing the lung may be used. A classifier for which machine learning has been performed to extract a lung region may be used.

The bronchus extracting unit 30 then extracts, as a three-dimensional bronchial region, a graph structure of the bronchial region included in the lung region extracted from the examination image V0. As a technique of extracting a bronchial region, for example, a technique of extracting a bronchial region by extracting a graph structure of bronchi using a Hessian matrix, classifying the extracted graph structure into a start point, an end point, a branch point, and a side, and connecting the start point, the end point, and the branch point by the sides, which is described in JP2010-220742A, can be used. Note that the technique of extracting the bronchial region is not limited to this one.

Figure 4:
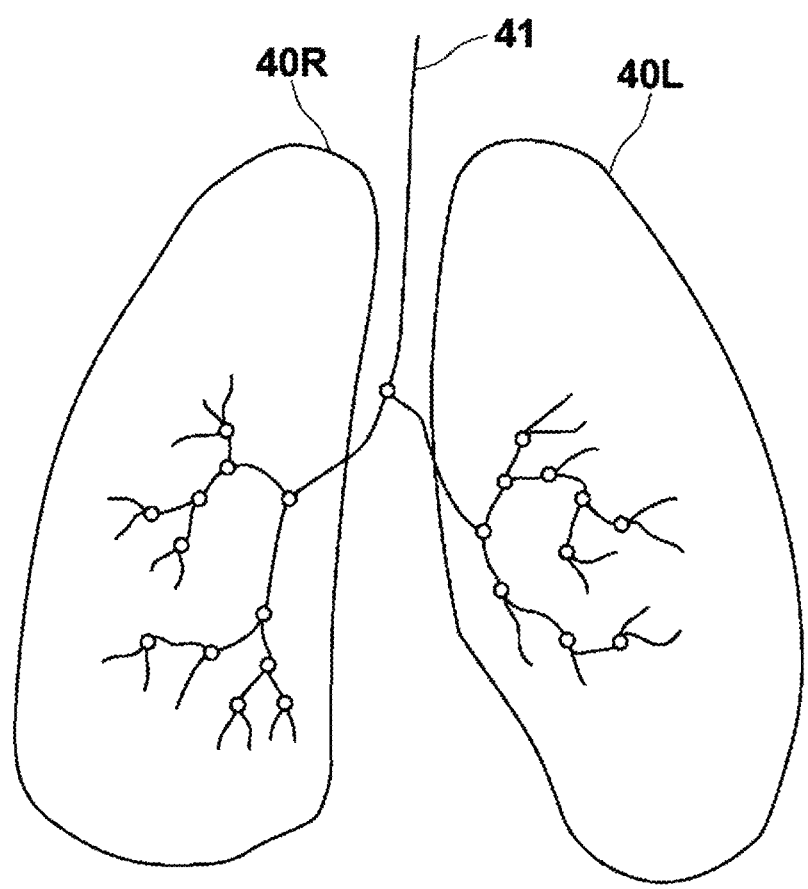
FIG. 4 is a diagram illustrating, along with lung regions, a graph structure in a bronchial region.

FIG. 4 is a diagram illustrating, along with lung regions, the graph structure in the bronchial region extracted by the bronchus extracting unit 30. As illustrated in FIG. 4, a left lung region 40L and a right lung region 40R include a graph structure 41 of the bronchi. In the graph structure 41, bronchi branches are represented by open dots.

Dividing a lung region into anatomical lung sections is diagnostically important. However, in a case of an advanced disease, the borders of the lung sections become unclear, thus making region division based on the lung sections difficult. In such a circumstance, if a lung region is divided in the up-down direction into three regions to have an equal volume, a change in region size due to expansion or contraction of a diseased region is distributed to the divided regions. Thus, the diseased region can no longer be recognized as a feature of the region. The bronchus included in the lung region branches into a bronchus directed toward the upper main body and a bronchus directed toward the lower main body. Therefore, dividing the lung region with reference to the bronchial branch position makes it easier to capture a partial change in the lung region of an advanced disease.

Figure 5:
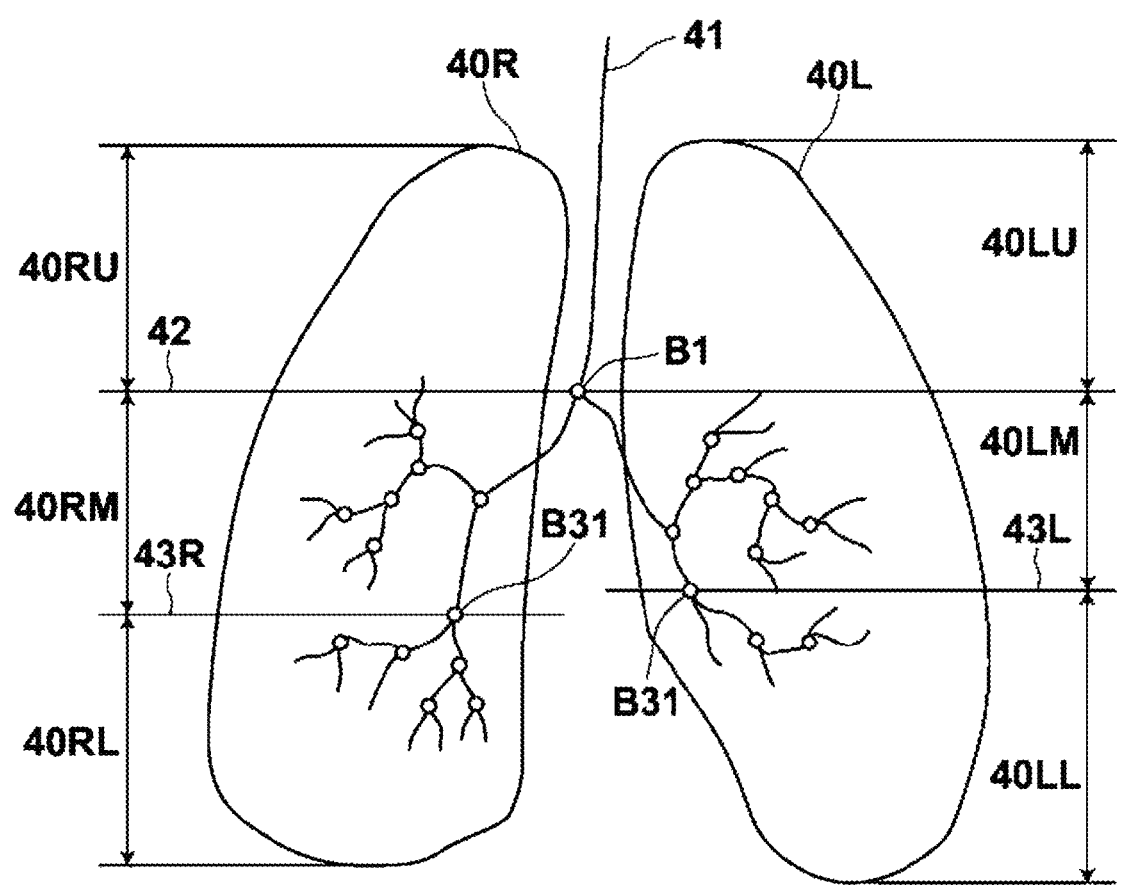
FIG. 5 is a diagram for describing a first division process performed by a first dividing unit.

Accordingly, the first dividing unit 31 divides, based on branch positions of a bronchus, a lung region into a plurality of regions in the up-down direction. Specifically, the first dividing unit 31 divides, with reference to a first bronchi branch and a third bronchi branch, each of a left lung region and a right lung region into three regions, i.e., an upper region, a middle region, and a lower region. FIG. 5 is a diagram for describing the first division process performed by the first dividing unit 31. There are two third bronchi branches in each of the left and right lung regions. It is assumed that the first dividing unit 31 performs region division with reference to the third bronchi branch located on a lower side in a body axis direction of the subject. As illustrated in FIG. 5, the first dividing unit 31 sets a horizontal plane 42 at a first bronchi branch B1, and sets horizontal planes 43L and 43R at respective third bronchi branches B31 located on the lower side in the left lung region 40L and the right lung region 40R, respectively. FIG. 5 illustrates the lung regions in two dimensions. However, since the examination image V0 is a three-dimensional image, horizontal planes are actually set in a manner as described above. The term "horizontal plane" refers to a plane perpendicular to the body axis of the subject for whom the examination image V0 is acquired.

The first dividing unit 31 divides the left lung region 40L into three regions, i.e., a left upper lung region 40LU between the horizontal plane 42 and the upper end of the left lung region 40L, a left middle lung region 40LM between the horizontal plane 42 and the horizontal plane 43L, and a left lower lung region 40LL between the horizontal plane 43L and the lower end of the left lung region 40L.

The first dividing unit 31 also divides the right lung region 40R into three regions, i.e., a right upper lung region 40RU between the horizontal plane 42 and the upper end of the right lung region 40R, a right middle lung region 40RM between the horizontal plane 42 and the horizontal plane 43R, and a right lower lung region 40RL between the horizontal plane 43R and the lower end of the right lung region 40R.

Since large bronchi and blood vessels are present in central regions of the lungs near the hilum of the lungs, the central regions are preferably distinguished from other regions mainly including the alveoli when the similarity between the examination image V0 and a case image is determined. Since the central regions of the lungs are also subjected to overall lung contraction and positional deviation due to the disease, the branch points of the bronchi are preferably used as references.

Figure 6:
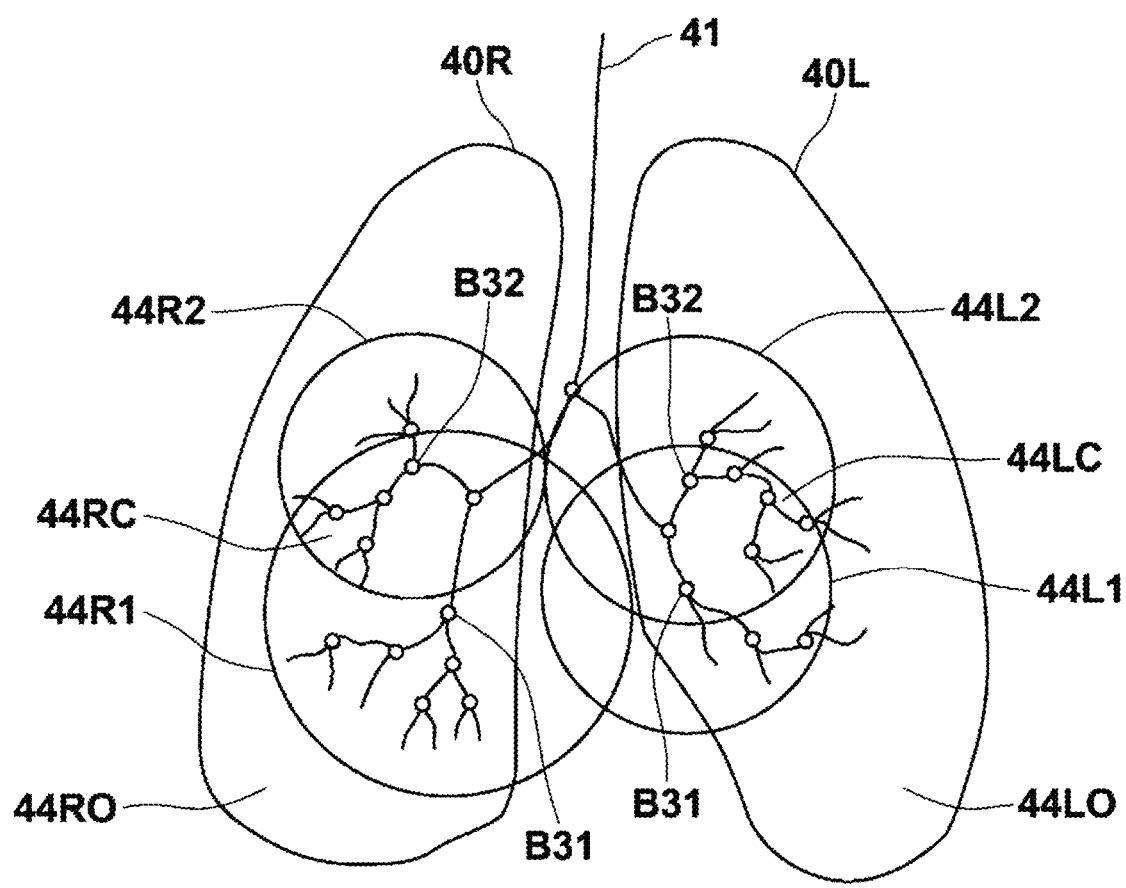
FIG. 6 is a diagram for describing a second division process performed by a second dividing unit.

The second dividing unit 32 divides the lung region into a region that is within a specific distance from a specific branch position among a plurality of branch positions and a region other than the region that is within the specific distance. Specifically, the second dividing unit 32 sets a spherical region having a specific radius from the third bronchi branch serving as the center in each of the left lung region 40L and the right lung region 40R. FIG. 6 is a diagram for describing the second division process performed by the second dividing unit 32. There are two third bronchi branches in each of the left and right lung regions. The second dividing unit 32 sets a spherical region having a specific radius at each of two third bronchi branches B31 and B32 in each of the left lung region 40L and the right lung region 40R. That is, as illustrated in FIG. 6, the second dividing unit 32 sets, in the left lung region 40L, a spherical region 44L1 centered at the third bronchi branch B31 located on the lower side and a spherical region 44L2 centered at the third bronchi branch B32 located on the upper side. The second dividing unit 32 also sets, in the right lung region 40R, a spherical region 44R1 centered at the third bronchi branch B31 located on the lower side and a spherical region 44R2 centered at the third bronchi branch B32 located on the upper side.

The radii of the spherical regions may be set according to the distances from the third bronchi branches B31 and B32 to the left and right ends of the left and right lung regions. For example, the radii of the spherical regions may be set to be 0.5 to 0.65 times the distances. In the right lung region 40R illustrated in FIG. 6, a distance from the third bronchi branch B31 to the right end of the right lung region 40R is greater than a distance from the third bronchi branch B32 to the right end of the right lung region 40R. Therefore, the radii of the spherical regions are such that the spherical region 44R1>the spherical region 44R2. On the other hand, in the left lung region 40L illustrated in FIG. 6, distances from the third bronchial branches B31 and B32 to the left end of the left lung region 40L are substantially equal. Therefore, the radii of the spherical regions are substantially equal for the spherical region 44L1 and the spherical region 44L2.

The second dividing unit 32 then divides the left lung region 40L into a left central region 44LC constituted by the spherical region 44L1 and the spherical region 44L2, and a region 44L0 other than the left central region 44LC.

The second dividing unit 32 also divides the right lung region 40R into a right central region 44RC constituted by the spherical region 44R1 and the spherical region 44R2, and a region 44R0 other than the right central region 44RC. The region 44L0 and the region 44R0 are regions mainly including the alveoli.

Figure 7:
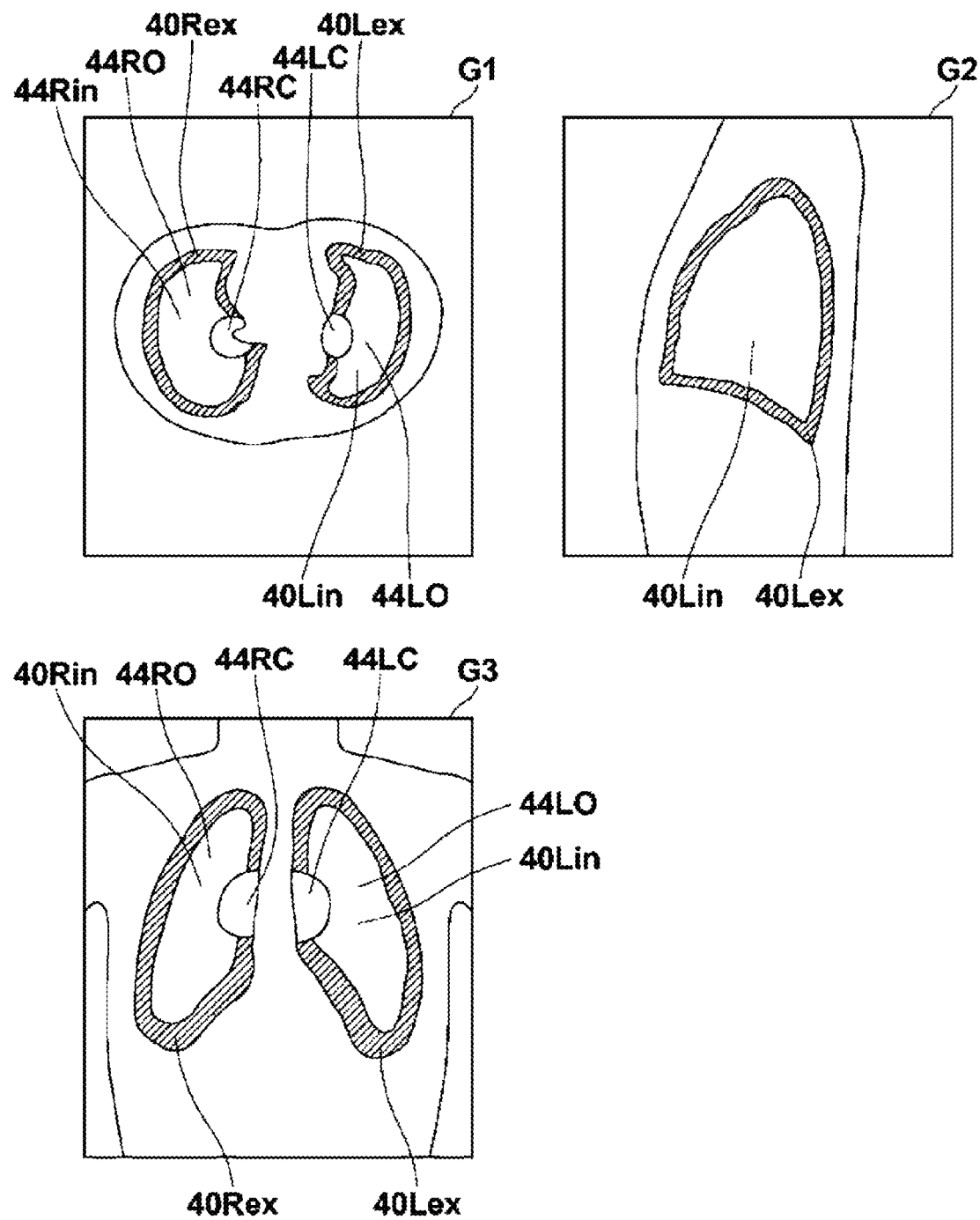
FIG. 7 is a diagram for describing a third division process performed by a third dividing unit.

The third dividing unit 33 divides the lung region into an outer region and an inner region. The third dividing unit 33 divides only the region 44L0 and the region 44R0 resulting from the division by the second dividing unit 32 into an outer region and an inner region. FIG. 7 is a diagram for describing the third division process performed by the third dividing unit 33. FIG. 7 illustrates a tomographic image G1 in an axial plane, a tomographic image G2 in a sagittal plane, and a tomographic image G3 in a coronal plane. The third dividing unit 33 divides the lung region into an outer region having a volume of 50% to 60% of the lung region from the pleura and an inner region other than the outer region. Specifically, the third dividing unit 33 divides the left lung region 40L into an outer region 40Lex and an inner region 40Lin, and divides the right lung region 40R into an outer region 40Rex and an inner region 40Rin.

The third dividing unit 33 divides each of the left upper lung region 40LU, the left middle lung region 40LM, the left lower lung region 40LL, the right upper lung region 40RU, the right middle lung region 40RM, and the right lower lung region 40RL resulting from the division by the first dividing unit 31 into an outer region and an inner region.

Figure 8:
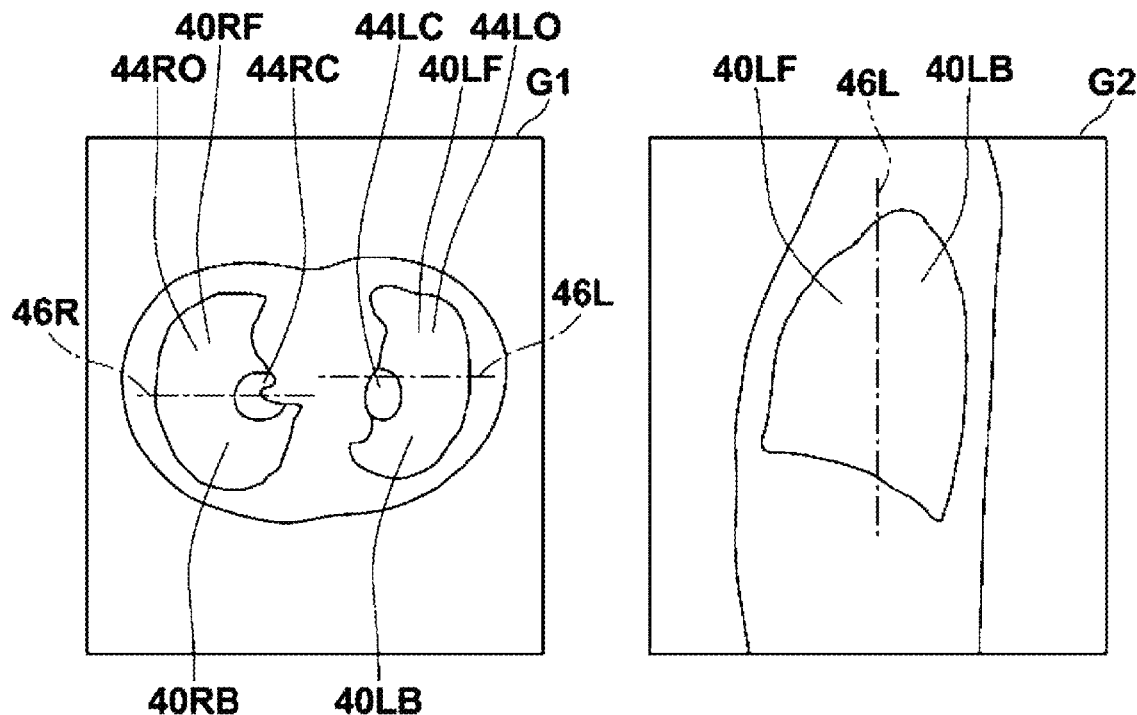
FIG. 8 is a diagram for describing a fourth division process performed by a fourth dividing unit.

The fourth dividing unit 34 divides the lung region into a dorsal region and a ventral region. The fourth dividing unit 34 divides only the region 44L0 and the region 44R0 resulting from the division by the second dividing unit 32 into a dorsal region and a ventral region. FIG. 8 is a diagram for describing the fourth division process performed by the fourth dividing unit 34. FIG. 8 illustrates the tomographic image G1 in the axial plane and the tomographic image G2 in the sagittal plane. The fourth dividing unit 34 divides the lung region into a dorsal region and a ventral region with reference to a coronal plane that equally divides the volume of the lung region into two. Specifically, the fourth dividing unit 34 sets a coronal cross-section 46L serving as a reference in the left lung region 40L, and divides the left lung region 40L into a dorsal region 40LB and a ventral region 40LF with reference to the coronal cross-section 46L. The fourth dividing unit 34 also sets a coronal cross-section 46R serving as a reference in the right lung region 40R, and divides the right lung region 40R into a dorsal region 40RB and a ventral region 40RF with reference to the coronal cross-section 46R.

The fourth dividing unit 34 further divides the outer region and the inner region, resulting from the division by the third dividing unit 33, of each of the left upper lung region 40LU, the left middle lung region 40LM, the left lower lung region 40LL, the right upper lung region 40RU, the right middle lung region 40RM, and the right lower lung region 40RL into a dorsal region and a ventral region.

Figure 9:
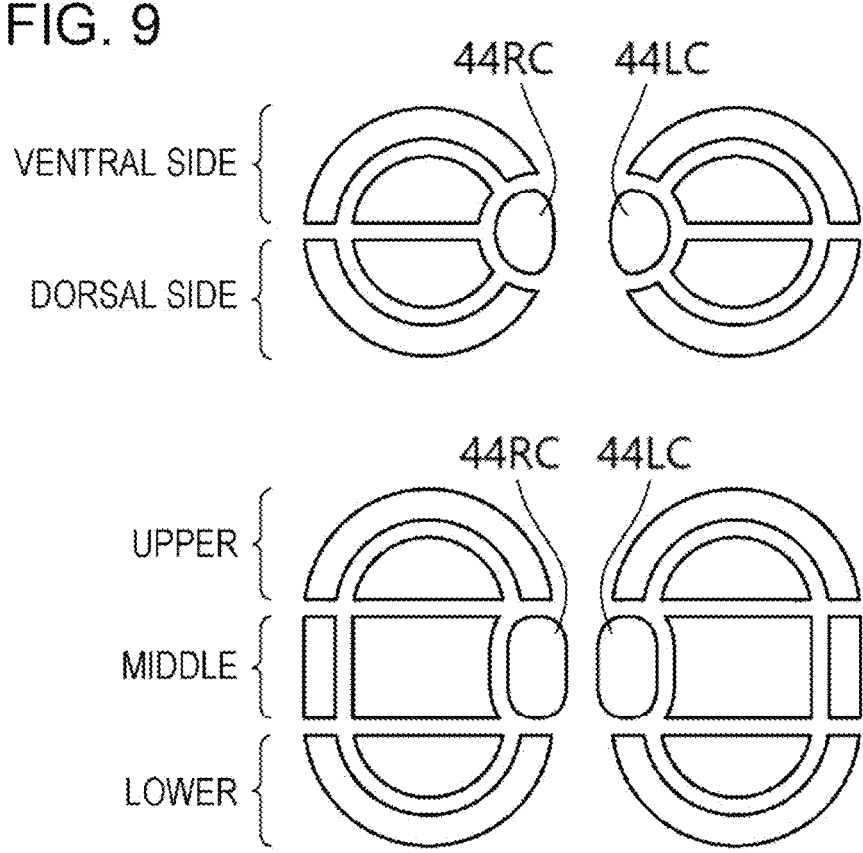
FIG. 9 is a diagram schematically illustrating a lung region division result obtained by the first dividing unit to the fourth dividing unit.

FIG. 9 is a diagram schematically illustrating a lung region division result obtained by the first dividing unit 31 to the fourth dividing unit 34. In FIG. 9, a diagram on the upper side illustrates an axial cross-section of the lung regions, and a lower diagram illustrates a coronal cross-section. In FIG. 9, only the left central region 44LC and the right central region 44RC are assigned reference numerals, and the reference numerals are omitted for the other regions obtained by the division. Each of the left and right lung regions is divided into thirteen regions as a result of the division performed by the first dividing unit 31 to the fourth dividing unit 34.

The division of the lung regions performed by the region dividing unit 22 is not limited to the first division to the fourth division described above. For example, as for interstitial pneumonia which is one of lung diseases, a lesion portion may spread around bronchi and blood vessels. Therefore, the bronchial region and the blood vessel region may be extracted from the lung region, and the lung region may be divided into a region of a predetermined range around the bronchial region and the blood vessel region and the other region. The predetermined range can be a region of a range of approximately 1 cm from the surfaces of bronchus and the blood vessel.

The findings classifying unit 23 classifies each of pixels of the lung region included in the examination image V0 into at least one of findings. Specifically, the findings classifying unit 23 calculates, for each pixel of the lung region included in the examination image V0, a plurality of evaluation values indicating possibilities of the pixel being respective types of tissues or lesions (that is, findings), and classifies each pixel of the examination image V0 into at least one finding type among the plurality of finding types based on the plurality of evaluation values. It is assumed in the present embodiment that the findings classifying unit 23 classifies each pixel of the examination image V0 into one finding.

The findings classifying unit 23 according to the present embodiment has a classifier constituted by a multilayer neural network generated through deep learning which is one type of mechanical learning. The findings classifying unit 23 identifies, using this classifier, the finding type to which each pixel of the examination image V0 belongs. The technique of machine learning is not limited to deep learning, and another technique such as a support vector machine may be used.

In the multilayer neural network, arithmetic processing is performed in each layer by using various kernels on data of a plurality of different feature quantities obtained at the previous layer. Further arithmetic processing is performed on data of the feature quantities obtained through this arithmetic processing in the next and subsequent layers. In this manner, the recognition rate of the feature quantities can be improved and the input data can be classified into a plurality of classes.

In the present embodiment, the multilayer neural network is described as a multilayer neural network that receives the examination image V0 as an input and outputs a result of classifying the lung region into a plurality of finding types. However, the multilayer neural network may be configured to receive, as an input, each of a plurality of examination slice images that constitute the examination image V0 and output a result of classifying the lung region into a plurality of finding types.

Figure 10:
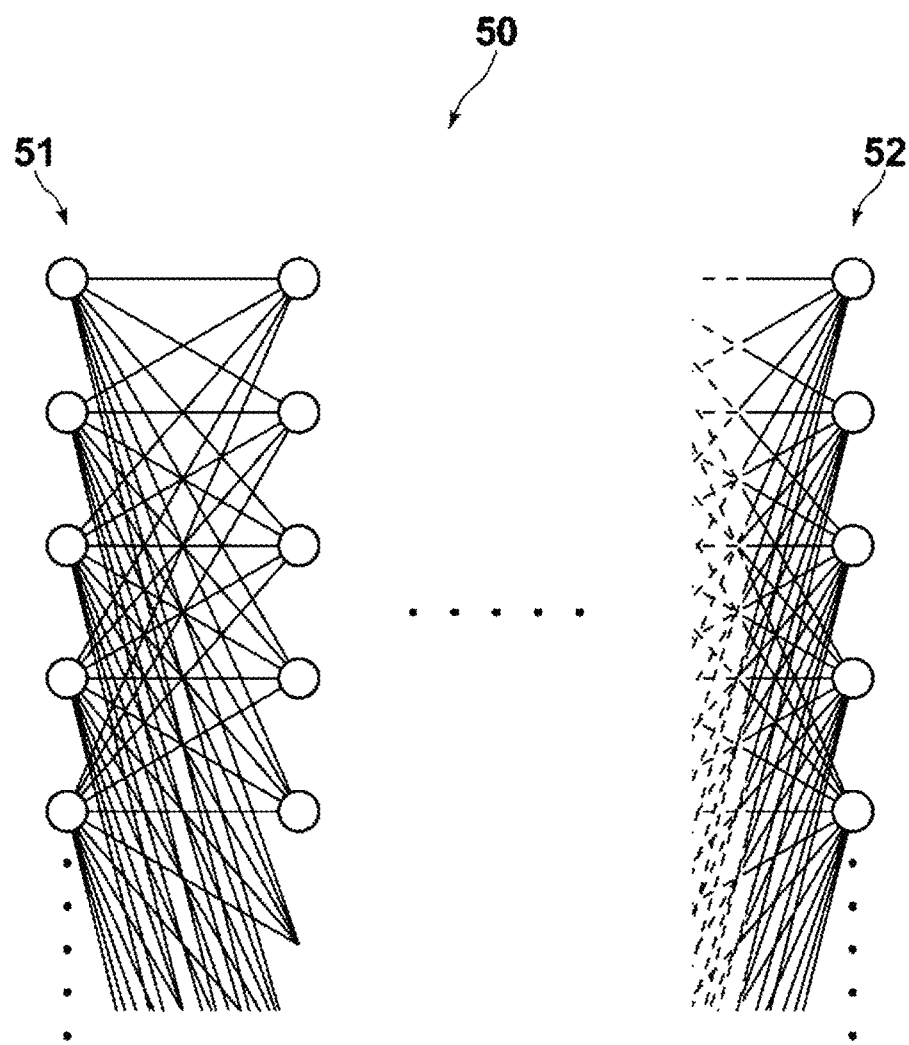
FIG. 10 is a diagram illustrating an example of a multi-layer neural network.

FIG. 10 is a diagram illustrating an example of a multilayer neural network. As illustrated in FIG. 10, a multilayer neural network 50 is constituted by a plurality of layers including an input layer 51 and an output layer 52. In the present embodiment, learning is performed to classify the lung region included in the examination image V0 into a plurality of findings such as an infiltrative shadow, a tumor shadow, a ground glass opacity, a centrilobular nodular shadow, a non-centrilobular nodular shadow, a dot shadow, a reticular shadow, a linear shadow, lobular interval wall thickening, a honeycomb lung, a cyst, a low-absorption region (emphysema), an emphysematous tendency, a cavity, pleural thickening, pleural effusion, bronchodilation, traction bronchodilation, blood vessels, a normal lung, a chest wall, and a mediastinum, for example. Note that the finding types are not limited to these types, and there may be more or less findings.

In the present embodiment, the multilayer neural network 50 performs learning using many pieces of training data, such as several millions of pieces of training data, of these findings. At the time of learning, a region of interest having a predetermined size (for example, 1.5 cm×1.5 cm) is cut out from a cross-sectional image for which the finding type is known, and the region of interest is used as training data. Then, the training data is input to the multilayer neural network 50 to cause the multilayer neural network 50 to output a result of finding type classification processing (hereinafter, referred to as a classification result). The output result is then compared with the training data. Depending on whether the output result is correct or incorrect, interlayer coupling weights of units (indicated by circles in FIG. 10) included in the individual layers of the multilayer neural network 50 are corrected from the output side toward the input side. Correction of the coupling weights is repeatedly performed using a large number of pieces of training data a predetermined number of times or until the correct answer rate of the output classification result reaches 100%. Then, learning is ended.

In a case where the input image is an examination slice image, a two-dimensional region normalized to a predetermined size (for example, 1.5 cm×1.5 cm) is cut out from the slice image constituting a three-dimensional image for which a lesion is known, and an image of the cut-out two-dimensional region is used as training data when the multilayer neural network 50 performs learning.

To perform classification, the findings classifying unit 23 extracts a lung region, which is a target region, from the examination image V0. The lung region may be extracted in substantially the same manner as the bronchus extracting unit 30 described above. The findings classifying unit 23 may use the lung region extracted by the bronchus extracting unit 30.

When performing the findings classification process, the findings classifying unit 23 sequentially cuts out regions of interest having the same size as that of the training data from the lung region of the examination image V0, and inputs the regions of interest to the classifier constituted by the multilayer neural network 50. Consequently, an evaluation value corresponding to each classification of the finding is output for the center pixel of the cut-out region of interest. The evaluation value corresponding to each classification is an evaluation value indicating the possibility of the center pixel belonging to the classification. A larger evaluation value indicates a higher possibility of the central pixel belonging to the classification.

FIG. 11 is a diagram illustrating evaluation values corresponding to respective finding types for a center pixel of a certain region of interest. For simplicity of explanation, FIG. 11 illustrates evaluation values for some of findings. In the present embodiment, the classifier classifies the center pixel of the region of interest into the finding assigned the largest evaluation value among the plurality of findings. For example, when evaluation values illustrated in FIG. 11 are acquired, the center pixel of the region of interest is most likely to be a reticular shadow and is next most likely to be a ground glass opacity. Conversely, there is little possibility of the normal lung or the low-absorption region. Therefore, when the evaluation values illustrated in FIG. 11 are acquired, the center pixel of the region of interest is classified into the reticular shadow assigned the largest evaluation value of 8.5 through the findings classification process. In this manner, every pixel of the lung region included in the examination image V0 is classified into any of the plurality of finding types.

In this manner, the findings classifying unit 23 classifies the center pixel of the region of interest input to the multilayer neural network 50 into the finding assigned the largest evaluation value among the plurality of evaluation values and generates a findings classification result. Thus, every pixel of the lung region included in the examination image V0 is classified into any of the plurality of finding types.

Figure 12:
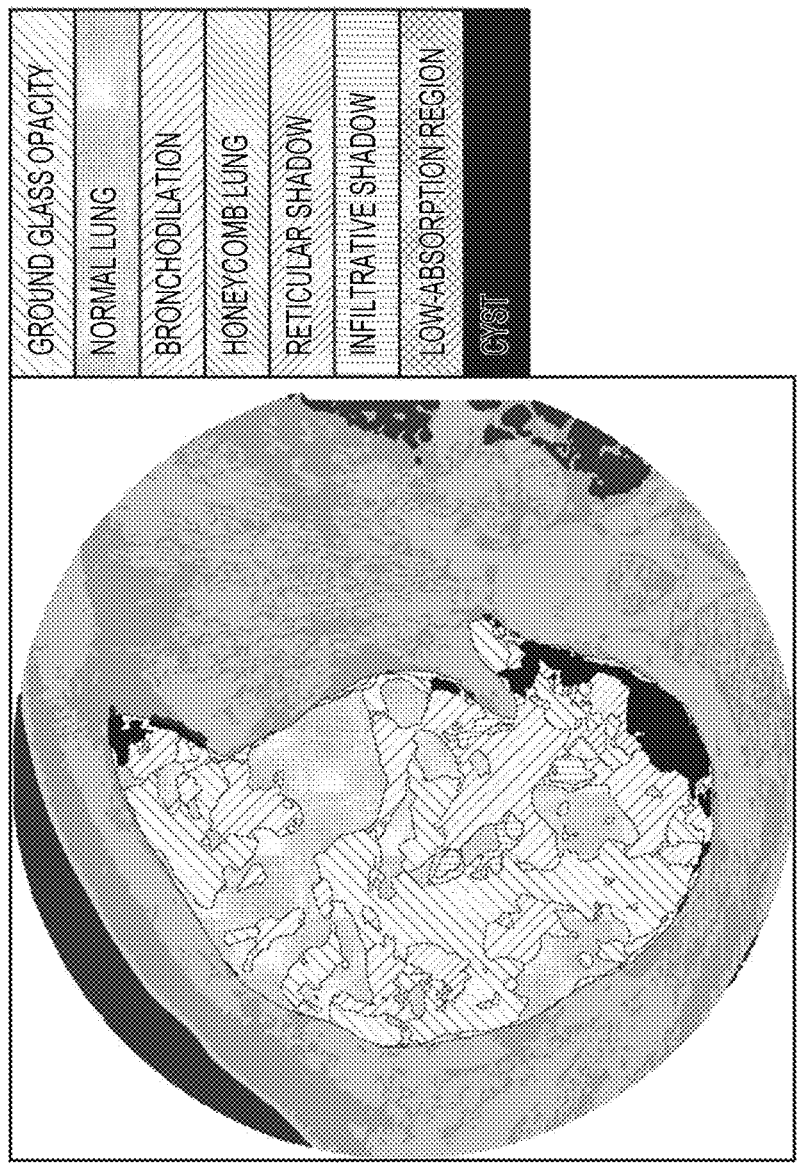
FIG. 12 is a diagram illustrating a cross section of a mapping image assigned colors corresponding to classifications.

The findings classifying unit 23 generates a mapping image by assigning a color to a region of each classification in the examination image V0 on the basis of the result of the findings classification process. Specifically, the findings classifying unit 23 generates a three-dimensional mapping image by assigning the same color to pixels classified into the same classification, for all pixels, in the three-dimensional space, each of which is classified into any of the plurality of finding types described above. FIG. 12 is a diagram illustrating a cross section of a mapping image assigned colors corresponding to respective classifications of a plurality of types. For simplicity of explanation, FIG. 12 illustrates a mapping image obtained when the pixels are classified into eight findings, i.e., the ground glass opacity, the normal lung, the bronchodilation, the honeycomb lung, the reticular shadow, the infiltrative shadow, the low-absorption region, and the cyst.

The mapping image may be displayed on the display unit 14 by the display control unit 28 described later. When the mapping image is displayed on the display unit 14, a cross-sectional image of any cross section of the three-dimensional mapping image may be displayed as illustrated in FIG. 12. However, the displayed image is not limited to this one, and the three-dimensional mapping image may be displayed on the display unit 14.

The feature quantity calculating unit 24 calculates feature quantities for respective findings classified in the examination image V0. Specifically, the feature quantity calculating unit 24 calculates, as a feature quantity, at least one of the size of the region of each finding, the average density of each finding, the dispersion of the density of each finding, the number of regions of each finding, the average size of the regions of each finding, and the like. A feature quantity calculated for the examination image V0 is referred to as a first feature quantity. The size of the region of each finding, the number of regions of each finding, the average size of the regions of each finding, or the like is a size feature quantity. As the size of the region of each finding, the volume of the region of each finding can be used.

In the case database DB described above, a file name, evaluation values of each pixel for a plurality of findings, and feature quantities for the respective findings are registered for each of a plurality of case images. A feature quantity registered in the case database DB for a case image is referred to as a second feature quantity. The first feature quantity and the second feature quantity are normalized to be have a value of 0 or greater and 1 or less. In response to acquisition of evaluation values of each pixel of the examination image V0 for a plurality of findings and feature quantities for the respective findings, the examination image V0 is registered as a new case image in the case database DB. At that time, the evaluation values and the first feature quantities of the examination image V0 are registered in the case database DB as the evaluation values and the second feature quantities of the new case image.

The region similarity deriving unit 25 derives, for each divided region, a region similarity between the examination image V0 and a case image, based on the first feature quantities calculated for the respective findings in the examination image V0 and the second feature quantities calculated in advance for the respective findings in the case image. The region similarity deriving unit 25 derives region similarities between each region of the examination image V0 and corresponding regions of all the case images registered in the case database DB.

For this purpose, the region similarity deriving unit 25 normalizes the first feature quantities calculated for the examination image V0 to have a value of 0 or greater and 1 or less. Then, as indicated by Equation (1) below, the region similarity deriving unit 25 calculates, for each finding, as a feature quantity difference Ddi, a difference in distance between the first feature quantity and the second feature quantity of the case image in each divided region. In Equation (1), i represents the finding type, k represents the feature quantity type, Tvk represents the first feature quantity for each type in the examination image V0, and Tck represents the second feature quantity for each type in the case image. The first feature quantity and the second feature quantity for which the difference is calculated are of the same type. In addition, in Equation (1), $\Sigma$ represents that the total sum of $(Tvk-Tck)^2$ for all the feature quantity types is determined. Since the first feature quantity and the second feature quantity are normalized to have a value of 0 or greater and 1 or less, the feature quantity difference Ddi also has a value of 0 or greater and 1 or less. When the first feature value Tvk and the second feature value Tck are equal to each other, the feature quantity difference Ddi is equal to 0. Instead of the difference in distance between the first feature quantity and the second feature quantity, the absolute value of the difference between the first feature quantity and the second feature quantity or the like may be used.

$$Ddi=\sqrt{(\Sigma(Tvk-Tck)^2)} \quad (1)$$

The region similarity deriving unit 25 then calculates a region similarity Sj0 between the examination image V0 and the case image using Equation (2) below. Specifically, the region similarity deriving unit 25 calculates, for each divided region, the region similarity Sj0 by adding the feature quantity differences Ddi for all the findings. In Equation (2), j represents the type of the divided region. When the region similarity Sj0 is calculated using Equation (2), the smaller the distance between the first feature quantity and the second feature quantity is, the more similar the corresponding regions in the examination image V0 and the case image are. Therefore, a negative sign is given to Equation (2), so that the value of the region similarity Sj0 increases as the examination image V0 and the case image are more similar to each other.

$$Sj0=-\Sigma Ddi \quad (2)$$

On the other hand, when the region similarity Sj0 is calculated using Equation (2), if the same findings have the same size, the region similarity Sj0 is equal to 0. However, when the same lesions are compared with each other, it is true that the larger the lesions are, the more similar the lesions are. When the region similarity Sj0 is calculated using Equation (2) above, there is no difference between a case where findings having a relatively large size have equal feature quantities and a case where findings having a relatively small size have equal feature quantities. This does not reflect the fact that as the sizes of the lesions become larger, the lesions are more similar to each other.

Therefore, the sizes of the same findings included in the divided regions of the examination image V0 and the case image are to not be handled simply as a difference. Instead, the region similarity is preferably increased as the sizes become more similar. Therefore, in the present embodiment, the region similarity deriving unit 25 further calculates, for each divided region, a size difference Dsi for each finding between the examination image V0 and the case image using Equation (3) below. In Equation (3), Pvi in each divided region represents a finding occupancy rate of a finding i in the examination image V0, and Pci represents a finding occupancy rate of the finding i in the case image.

$$Dsi=1-|Pvi-Pci|/(Pvi+Pci) \quad (3)$$

Therefore, the region similarity deriving unit 25 preferably calculates a region similarity Sj1 between the examination image V0 and the case image using Equation (4) below. The value of Ddi decreases as the feature value of the finding in each divided region of the examination image V0 and the feature value of the finding in the corresponding divided region of the case image become more similar to each other. The value of Dsi increases as the size of the finding in each divided region of the examination image V0 and the size of the finding in the corresponding divided region of the case image become more similar to each other. Therefore, by using Equation (4), the region similarity Sj1 that has a larger value as the corresponding regions in the examination image V0 and the case image are more similar to each other can be calculated in consideration of the sizes of the same findings.

$$Sj1=\Sigma(Dsi-Ddi) \quad (4)$$

The finding occupancy rate is calculated in the following manner. First, the region similarity deriving unit 25 calculates the volume of each finding i in each divided region. The volume of each finding can be calculated by multiplying the number of pixels of the finding included in each region by a volume per voxel of the examination image V0. FIG. 13 illustrates calculation results of volumes of findings. In FIG. 13, the unit of volume is cubic millimeters. The region similarity deriving unit 25 then normalizes the volume of the finding by the volume of each region to calculate the finding occupancy rate (=finding volume/lung volume). Note that the finding occupancy rate may be included in the first feature quantities as the size feature quantity and may be calculated by the feature quantity calculating unit 24.

When the region similarity Sj1 is calculated using Equation (4), the maximum value of the region similarity Sj1 changes from divided region to divided region in the examination image V0. Therefore, the region similarity Sj1 is preferably normalized in accordance with a condition that the region similarity Sj1 between the corresponding regions of the examination image V0 and the case image is maximum, that is, a condition that there is no difference between the corresponding regions of the examination image V0 and the case image. Equation (5) is obtained by normalizing the region similarity Sj1 calculated using Equation (4) by a condition Sj max that the region similarity Sj1 between the corresponding regions of the examination image V0 and the case image is maximum. In Equation (5), Sj2 represents the normalized region similarity.

$$Sj2=Sj1/Sj\ \text{max}=\Sigma(Dsi-Ddi)/Sj\ \text{max} \quad (5)$$

The region similarity Sj0 is also preferably normalized when the region similarity is calculated using Equation (2).

Equation (6) is obtained by normalizing Equation (2) in accordance with a condition that the region similarity $Sj0$ between the corresponding regions of the examination image V0 and the case image is maximum. In Equation (6), $Sj3$ represents the normalized region similarity.

$$Sj3 = Sj0/Sj \max = \Sigma Dsi/Sj \max \qquad (6)$$

The similarity deriving unit 26 derives the similarity between the examination image V0 and the case image by performing a weighted calculation on the plurality of region similarities using respective weight coefficients based on at least one of sizes of the respective divided regions or sizes of a specific finding included in the respective divided regions. It is assumed that the similarity deriving unit 26 derives the similarity between the examination image V0 and the case image using the region similarities $Sj2$.

As for pulmonary fibrosis or the like of lung diseases, findings of the reticular shadow and the honeycomb lung tend to occur predominantly on the lower side of the lung and predominantly directly below the pleura. Conversely, in the initial stage of general bacterial pneumonia, a shadow does not occur directly below the pleura but the ground glass opacity and the infiltrative shadow develop from the inner side. In addition, in the case of aspiration pneumonia or the like, the shadow is likely to occur on the dorsal side of the lung. As described above, the lung diseases have characteristic onset positions for the respective diseases in the lungs. In order to derive the similarity between the examination image V0 and the case image in consideration of such characteristics of the onset positions, the region similarities $Sj2$ derived for the respective divided regions are added for all the regions. In this manner, the similarity between the examination image V0 and the case image can be derived in consideration of the similarity in the onset position of the disease.

However, as described above, the sizes of the divided regions resulting from the division by the region dividing unit 22 are different from region to region. To derive the similarity independently from the size of the region, the region similarity $Sj2$ may be weighted by the size of the divided region. In addition, there is a medically important region or the like. The weight for such an important region is preferably increased.

In general, the similarity is derived mainly for a lesion to search for a case image. Therefore, the region in which the lesion is present is an important region. The similarity between the examination image V0 and the case image can be derived while placing emphasis on the lesion by normalizing the size of the lesion in each divided region of the examination image V0 by the size of the lesion in the entire lung region and by performing weighting corresponding to a lesion percentage thus obtained on the region similarity $Sj2$. By deriving the similarity in this way, a case image desired by a doctor can searched for.

For example, suppose that the lung region is divided into ten regions. Suppose that nine regions among the ten divided regions are in a normal state and a lesion is present in one region. In such a case, in the case where all the region similarities derived for the ten regions are equal to 0.9, if all the regions are equally evaluated, the similarity between the examination image V0 and the case image is equal to 9.0. On the other hand, in the case where all the region similarities derived for the nine regions that are in the normal state among the ten regions are equal to 1.0 and the region similarity derived for the region in which the lesion is present is 0, if all the regions are equally evaluated, the similarity between the examination image V0 and the case image is equal to 9.0 which is equal to the similarity derived in the case where all the region similarities derived for the ten regions are equal to 0.9. Therefore, by increasing the weight for the region similarity of the region in which the lesion is present and decreasing the weight for the region similarity of the normal region, the similarity can be derived in consideration of the region in which the lesion is present.

Therefore, in the present embodiment, the similarity deriving unit 26 classifies the plurality of finding types into a findings group serving as a background (hereinafter, referred to as a background findings group) such as the normal lung and the emphysematous tendency, and a findings group serving as a lesion (hereinafter, referred to as a lesion findings group) such as the dot shadow, the ground glass opacity, and the infiltrative shadow. The similarity deriving unit 26 calculates a weight coefficient $Wj$ used in deriving the similarity between the examination image V0 and the case image, by using only findings classified into the lesion findings group. Specifically, the similarity deriving unit 26 calculates the weight coefficient $Wj$ for each region using Equation (7) below. In Equation (7), $Aj$ represents the size of a region j, and $Pv1ij$ represents a finding occupancy rate of all the findings classified into the lesion findings group in the region j. Note that $Aj$ may be used as the weight coefficient $Wj$, or $Pv1ij$ may be used as the weight coefficient $Wj$.

$$Wj = Aj \times Pv1ij \qquad (7)$$

The similarity deriving unit 26 calculates a similarity $St$ between the examination image V0 and the case image using the weight coefficients $Wj$ calculated based on Equation (7) and using Equation (8) below. In Equation (8), $B0$ is a value obtained by multiplying the size of the entire lung region by the finding occupancy rate of all the findings classified into the lesion findings group in the lung region.

$$St = \Sigma(Wj \times Sj2)/B0 \qquad (8)$$

On the other hand, the degrees of importance of findings that are classified into a lesion also change from finding type to finding type. For this reason, the similarity is preferably derived in consideration of the degrees of importance of the findings. Therefore, the similarity deriving unit 26 sets a degree of importance $Ii$ for each finding using Equation (9) below. In Equation (9), i represents the finding type that is classified as a lesion, and fi represents a function having, as a parameter, the finding occupancy rate $Pvi$ for each finding classified as a lesion in each divided region of the examination image V0.

$$Ii = fi(Pvi) \qquad (9)$$

As illustrated in FIG. 13, the number of digits of the value of the volume is different between a finding having a large size and a finding having a small size. Therefore, the dimension is preferably decreased by converting the finding occupancy rate, which is three-dimensional information, into information equivalent to two dimensions using the function fi. This makes the difference in the size of the finding match the sense of the doctor. Therefore, as described above, the finding having a small size but having a high degree of importance is preferably nonlinearly converted using the function fi in order to increase the degree of importance. Thus, in the present embodiment, the function fi is set as indicated by Equation (10) below.

$$fi = a \cdot (b \cdot X + (1-b) \cdot X^c) \qquad (10)$$

In Equation (10), a is a constant that determines the difference in overall importance of each finding. c is a constant that takes a value of 1 or less and determines the effect of emphasizing a finding having a small size. b is a constant that determines the degree of the effect of the constant c. In addition, $X=(Pvi)^{2/3}$ holds. By raising the finding occupancy rate Pvi to the power of 2/3, the finding occupancy rate Pvi is converted from a value equivalent to three dimensions to a value equivalent to two dimensions.

The similarity deriving unit 26 sets the degree of importance Iij for each of the findings classified into the lesion for each of the divided regions by setting the function represented by Equation (10) for the finding and by applying the function to Equation (9). As indicated by Equation (11) below, the similarity deriving unit 26 then calculates the total sum of the degrees of importance Iij thus set in the region, and multiplies the total sum by the size Aj of the region to calculate the weight coefficient W1j. Note that ΣIij may be used as the weight coefficient W1j.

$$W1j = Aj \times \Sigma Iij \quad (11)$$

The similarity deriving unit 26 then calculates the similarity St between the examination image V0 and the case image using the weight coefficients W1j calculated based on Equation (11) and using Equation (12) below. In Equation (12), B1 is a value obtained by multiplying the size of the entire lung region by the total sum of the degrees of importance Iij of all the findings classified into the lesion findings group in the lung region.

$$St = \Sigma(W1j \times Sj2)/B1 \quad (12)$$

The search unit 27 performs a search process of searching for, as a similar case image, a case image that is similar to the examination image V0 from the case database DB based on the similarities St. The case database DB will be described first.

In the case database DB, a plurality of case images constituted by one or more case slice images are registered. Specifically, the findings classification result and the feature quantities (that is, the second feature quantities) of each of the plurality of case images are registered in association with the case image among the plurality of case images. In the present embodiment, when the examination image V0 is newly acquired, the examination image V0 is registered as a new case image in the case database DB.

Based on the similarities St between the examination image V0 and all the case images registered in the case database DB, the search unit 27 searches for a case image similar to the examination image V0 as a similar case image. Specifically, the search unit 27 sorts the case images in descending order of the similarity St and creates a search result list. FIG. 14 is a diagram illustrating the search result list. As illustrated in FIG. 14, the case images registered in the case database DB are sorted in descending order of the similarity St in a search result list L0. The search unit 27 extracts from the case database DB as similar case images, a predetermined number of case images from the top in the sorted order in the search result list L0.

Figure 15:
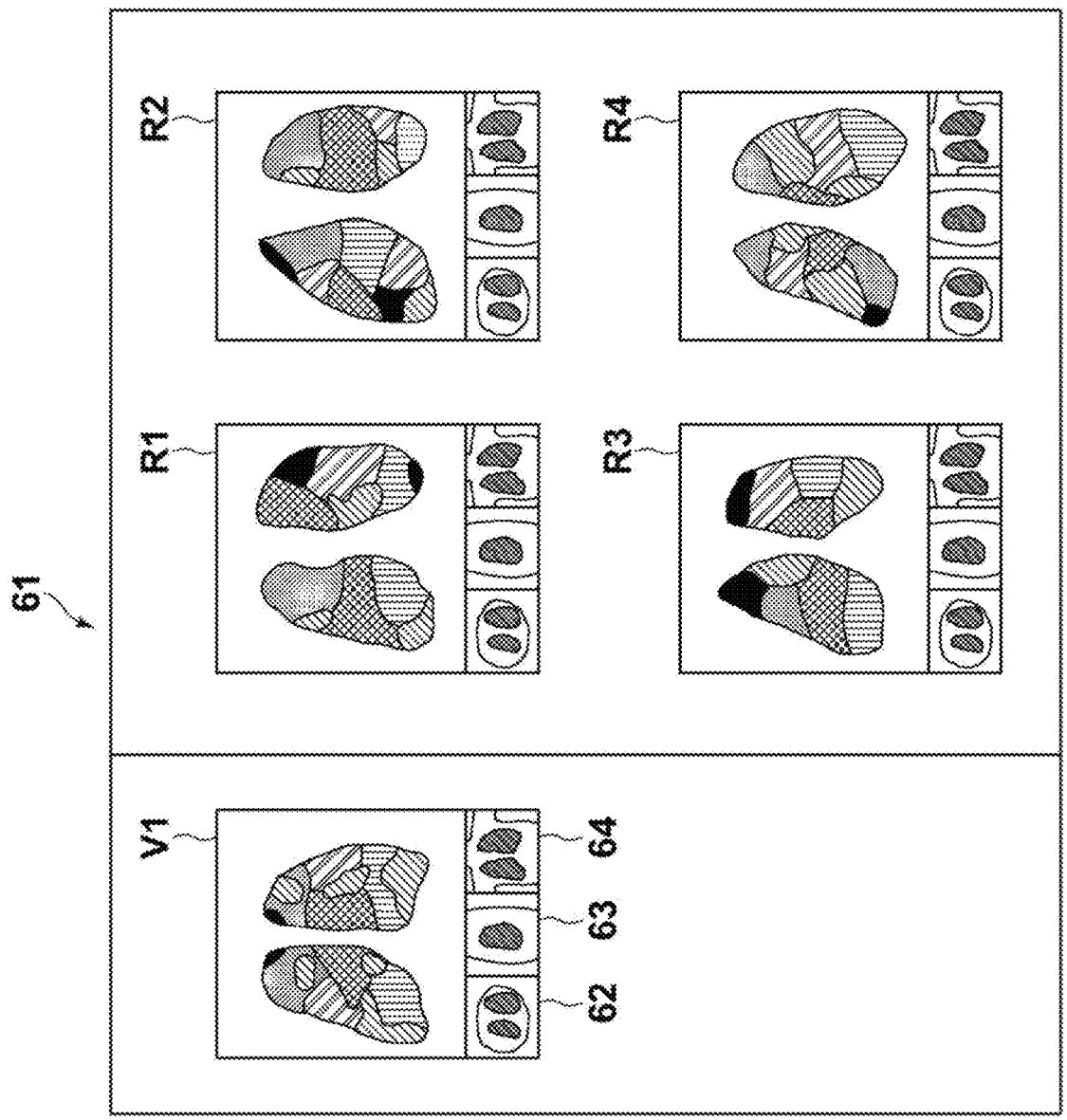
FIG. 15 is a diagram illustrating a search result.

The display control unit 28 displays the search result obtained by the search unit 27 on the display unit 14. FIG. 15 is a diagram illustrating the search result. As illustrated in FIG. 15, a labeled examination image V1 and labeled similar case images R1 to R4 are displayed in a search result 61. Although four similar case images R1 to R4 are displayed here, more similar case images may be displayed.

In FIG. 15, the examination image V1 and the similar case images R1 to R4 are projection images projected by a predetermined projection method. Although only five types of labeling are illustrated in FIG. 15 for explanation, labeling corresponding to each of the classified finding types is actually performed. Examination slice images 62 to 64 in three cross-sections, i.e., an axial cross-section, a sagittal cross-section, and a coronal cross-section, are displayed below the examination image V1. Case slice images in three similar cross-sections are also displayed below the similar case images R1 to R4. The slice planes of the examination slice images 62 to 64 displayed below the examination image V1 and of the case slice images displayed below the similar case images R1 to R4 can be switched by an operation on the input unit 15.

Figure 16:
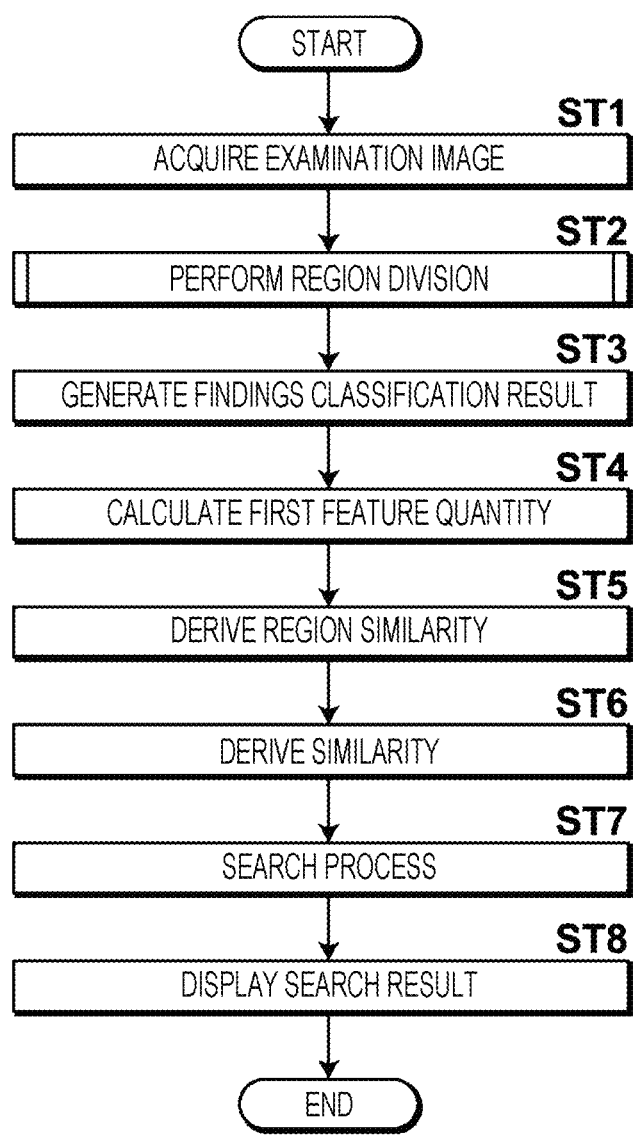
FIG. 16 is a flowchart illustrating a process performed in the first embodiment.

A process performed in the first embodiment will be described next. FIG. 16 is a flowchart illustrating a process performed in the first embodiment. First, the image acquiring unit 21 acquires the examination image V0 (step ST1). The region dividing unit 22 divides a lung region in the examination image V0 into a plurality of regions (step ST2).

Figure 17:
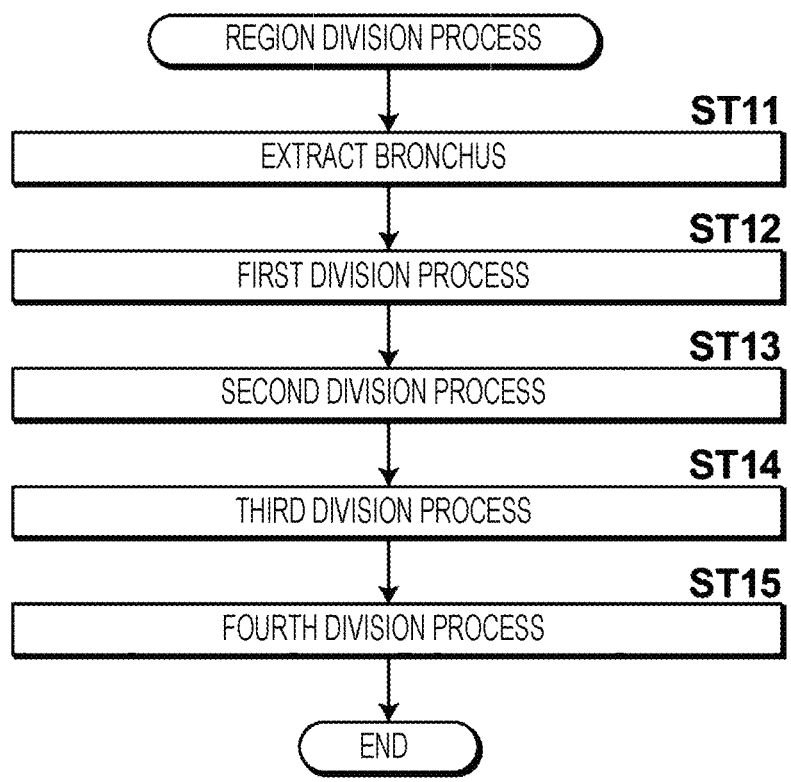
FIG. 17 is a flowchart of a region division process.

FIG. 17 is a flowchart of the region division process. In the region division process, the bronchus extracting unit 30 extracts the bronchial structure from the examination image V0 as a bronchial region (step ST11). The first dividing unit 31 then divides, based on branch positions of the bronchi, the lung region into a plurality of regions in the up-down direction (first division process; step ST12). The second dividing unit 32 also divides the lung region into a central region and a region other than the central region (second division process; step ST13). The third dividing unit 33 also divides the lung region into an outer region and an inner region (third division process; step ST14). The fourth dividing unit 34 then divides the lung region into a dorsal region and a ventral region (fourth division process; step ST15). The region division process then ends.

Referring back to FIG. 16, the findings classifying unit 23 classifies each pixel of the lung region included in the examination image V0 into at least one of findings and generates a findings classification result (step ST3). The feature quantity calculating unit 24 then calculates, for each of the divided regions, the first feature quantities for the respective findings classified in the examination image V0 (step ST4). Based on the first feature quantities calculated for the respective findings in the examination image V0 and the second feature quantities calculated in advance for the respective findings in the case image, the region similarity deriving unit 25 derives a region similarity which is a similarity between each divided region of the examination image V0 and the corresponding divided region of the case image (step ST5). The similarity deriving unit 26 performs a weighted calculation on the plurality of region similarities to derive the similarity between the examination image V0 and the case image (step ST6). As described above, the similarity deriving unit 26 derives the similarities between the examination image V0 and all the case images registered in the case database DB. Further, the search unit 27 performs the search process based on the similarities (step ST7). The display control unit 28 displays the search result on the display unit 14 (step ST8). The process then ends.

As described above, according to the present embodiment, a lung region in the examination image V0 is divided into a plurality of regions, and each of pixels of the examination image V0 is classified into at least one of findings. The first feature quantities for the respective findings classified in the examination image V0 are calculated for each divided region. Based on the first feature quantities calculated for the respective findings in the examination image V0 and the second feature quantities calculated in advance for the respective findings in a case image, the region similarity between the examination image V0 and the case image is derived for each of the divided regions. The similarity between the examination image V0 and the case image is derived by performing a weighted calculation on the plurality of region similarities using weight coefficients based on at least one of sizes of the respective divided regions or sizes of a specific finding included in the respective divided regions. According to the present embodiment, the weighted calculation is performed on the region similarities for the respective divided regions as described above. Thus, the similarity between the examination image V0 and the case image can be appropriately determined by appropriately performing weighting according to the positions and distributions of the findings in the target region.

In particular, in the region division process, the bronchi are extracted from a lung region included in the examination image V0. A plurality of branch positions of the bronchi are identified. Based on the identified branch positions, the lung region is divided into a plurality of regions. Therefore, according to the present embodiment, the lung region can be divided based on the branch positions of the bronchi independently from the lung sections and independently from the predetermined percentages. Thus, the lung region can be appropriately divided.

A second embodiment of the present disclosure will be described next. In the first embodiment described above, the similarity between the examination image V0 and the case image is derived by deriving the region similarities for thirteen regions on each of the left and right sides obtained by the division by the region dividing unit 22. The second embodiment differs from the first embodiment in that a lung region is divided, based on a plurality of types of region patterns different from one another, into a plurality of regions for each of the region patterns and the region similarities are derived for each of the region patterns. Note that the configuration of a similarity determining apparatus according to the second embodiment is the same as that of the similarity determining apparatus according to the first embodiment and only a process to be performed is different. Thus, detailed description of the apparatus is omitted herein.

When an onset position of a disease in the lungs is a position characteristic to the disease and extends over a relatively wide range, the similarity between the examination image V0 and the case image can be appropriately derived even if the lung region is divided according to one region pattern as in the first embodiment described above. However, in the case of a lesion, such as a tumor lesion, that occurs locally and occurs at various positions in the lung region, even if the lesion is present in both the examination image V0 and the case image, the value of the similarity is not large unless the lesion is present in the corresponding regions of the examination image V0 and the case image. As a result, a case image similar to the examination image V0 cannot be searched for.

In general, a local lesion that occurs locally and a diffuse lesion have different characteristics. Therefore, these lesions are classified into different findings. For example, findings such as the ground glass opacity and the reticular shadow are diffuse lesions, and findings such as the nodular shadow are local lesions. In the case of findings classified into diffuse lesions, the similarity between the examination image V0 and the case image can be appropriately derived by deriving the region similarities for respective divided regions obtained by dividing the lung region more finely. On the other hand, in the case of findings classified into local lesions, the similarity between the examination image V0 and the case image can be appropriately derived by deriving the region similarities for respective regions obtained by dividing the lung region coarsely.

Therefore, in the second embodiment, region similarities are determined based not only on a region pattern (hereinafter, referred to as a first region pattern) for dividing each of the left and right lung regions into thirteen regions as in the first embodiment but also on a pattern (hereinafter, referred to as a second region pattern) of divided regions obtained by performing only the first division process by the first dividing unit 31, a pattern (hereinafter, referred to as a third region pattern) of divided regions obtained by performing only the second division process by the second dividing unit 32, a pattern (hereinafter, referred to as a fourth region pattern) of divided regions obtained by performing only the third division process by the third dividing unit 33, and a pattern (hereinafter, referred to as a fifth region pattern) of divided regions obtained by performing the fourth division process by the fourth dividing unit 34.

In the second embodiment, a state in which the left lung region 40L and the right lung region 40R are not divided at all is also included in one of the region patterns (sixth region pattern).

In the second embodiment, it is not necessary to use all of the first to sixth region patterns, and it is sufficient to divide the left lung region 40L and the right lung region 40R based on two or more of these region patterns. One lung region is divided into thirteen regions according to the first region pattern, three regions according to the second region pattern, two regions according to the third region pattern, two regions according to the fourth region pattern, two regions according to the fifth region pattern, and one region according to the sixth region pattern. Therefore, when all of the first to sixth region patterns are used, 23 region similarities are derived for one lung region (46 for the left and right lungs).

In the second embodiment, the similarity deriving unit 26 calculates a weight coefficient W2j for each region using Equation (13) below with respect to the region similarities based on all the region patterns. In Equation (13), Iij represents the degree of importance of each finding classified into a lesion for each divided region, and PWir is a weight coefficient for the finding i included in the divided region resulting from the division according to a region pattern r. Therefore, with Equation (13), the weight coefficient W2j is calculated by calculating the total sum of the values obtained by weighting the degree of importance Iij of the finding for each divided region by the weight coefficient PWir for the finding i corresponding to the region pattern in the region and by multiplying the total sum by the size Aj of the region. The weight coefficient PWir represents a region pattern weight coefficient. Σ(Pwir×Iij) may be used as the weight coefficient W2j.

$$W2j = Aj \times \Sigma(Pwir \times Iij) \tag{13}$$

FIG. 18 is a diagram illustrating an example of the weight coefficient PWir. In FIG. 18, "FIRST", "SECOND", and "SIXTH" indicate the first region pattern (one lung is divided into thirteen regions), the second region pattern (one lung is divided into three regions), and the sixth region pattern (one lung is divided into one region), respectively. As illustrated in FIG. 18, for example, 0.7 is set as the weight coefficient PWir for the finding of the ground glass opacity included in the divided region obtained according to the first region pattern. In addition, 0.3 is set as the weight coefficient PWir for the finding of the ground glass opacity included in the divided region obtained according to the second region pattern. In addition, 0 is set as the weight coefficient PWir for the finding of the ground glass opacity included in the divided region obtained according to the sixth region pattern. When the weight coefficient PWir is equal to 0, the weight coefficient W2j calculated using Equation (13) is also equal to 0. On the other hand, 0 is set as the weight coefficient PWir for the finding of the nodular shadow included in the divided region obtained according to the first region pattern. In addition, 0.5 is set as the weight coefficient PWir for the finding of the nodular shadow included in the divided region obtained according to the second region pattern. In addition, 0.5 is set as the weight coefficient PWir for the finding of the nodular shadow included in the divided region obtained according to the sixth region pattern.

Therefore, by adopting the weight coefficient PWir illustrated in FIG. 18, when the similarity St is derived, the region similarities for the fine divided regions are mainly adopted for the findings of the ground glass opacity and the reticular shadow, and the region similarities for the coarse divided regions are mainly adopted for the findings of the nodular shadow. Consequently, the similarity St between the examination image V0 and the case image can be derived in consideration of the characteristics of local lesions and diffuse lesions.

In the second embodiment, the similarity deriving unit 26 calculates the similarity St between the examination image V0 and the case image using the weight coefficients W2j calculated based on Equation (13) and using Equation (14) below. In Equation (14), B3 is a value obtained by multiplying the size of the entire lung region by the total sum of W2j for all the findings classified into the lesion findings group in the lung region.

$$St = \Sigma(W2j \times Sj2)/B3 \quad (14)$$

In the second embodiment, the weight coefficient PWir may be changed. For example, the weight coefficient PWir may be changed depending on whether the lesion of interest in the examination image V0 is local or diffuse. In this case, the weight coefficient PWir may be preferably changed in response to a change instruction given by an operator on the input unit 15. FIGS. 19 and 20 are diagrams illustrating other examples of the weight coefficient PWir. The weight coefficient PWir illustrated in FIG. 19 has a value of 0 for all the findings in the case of the sixth region pattern. By using such a weight coefficient PWir, a similar case image can be appropriately searched for in the case where a lesion of interest in the examination image V0 is only a local lesion.

On the other hand, the weight coefficient PWir illustrated in FIG. 20 has a value of 0 for all the findings in the case of the first region pattern. By using such a weight coefficient PWir, a similar case image can be appropriately searched for in the case where a lesion of interest in the examination image V0 is only a diffuse lesion.

In each of the embodiments described above, the region similarity between corresponding regions in the examination image V0 and the case image is derived. However, the region similarity is not limited this one. For example, not only the region similarity between the corresponding regions but also the region similarity between regions other than the corresponding regions may be derived. When the region similarity between a region and a region other than the corresponding region is derived, the weight is preferably increased as the region is closer to the corresponding region.

In each of the embodiments described above, a plurality of evaluation values indicating the possibilities of each pixel of the examination image V0 being respective finding types are calculated, and each pixel of the first medical image V0 is classified into at least one of the plurality of finding types based on the plurality of evaluation values. However, the findings classification technique is not limited to a technique using the evaluation values.

In each of the embodiments described above, the case database DB is stored in the image storage server 3. However, the case database DB may be stored in the storage 13.

In each of the embodiments described above, the examination image is registered in the case database DB. However, an image other than the examination image may be registered in the case database DB as a registration-target image.

In addition, in the embodiments described above, only the region dividing unit 22, the findings classifying unit 23, the feature quantity calculating unit 24, and the display control unit 28 in the similarity determining apparatus may be used as a feature quantity deriving apparatus. In this case, a feature quantity deriving program causes the CPU 11 to execute the region division process, the findings classification process, the feature quantity calculation process, and the display control process. By displaying the derived feature quantities on the display unit 14, an operator such as a doctor can recognize the feature quantities of the findings of the lung region included in the examination image V0.

In each of the embodiments described above, various processors described below can be used as the hardware structure of processing units that execute various processes, such as the image acquiring unit 21, the region dividing unit 22, the findings classifying unit 23, the feature quantity calculating unit 24, the region similarity deriving unit 25, the similarity deriving unit 26, the search unit 27, the display control unit 28, the bronchus extracting unit 30, the first dividing unit 31, the second dividing unit 32, the third dividing unit 33, and the fourth dividing unit 34, for example. The aforementioned various processors include, in addition to a CPU which is a general-purpose processor that executes software (program) to function as the various processing units, a PLD (Programmable Logic Device), such as an FPGA (Field Programmable Gate Array), which is a processor whose circuitry is changeable after production, a dedicated electric circuit, such as an ASIC (Application Specific Integrated Circuit), which is a processor having circuitry designed specifically for executing specific processing, and the like.

One processing unit may be constituted by one of these various processors, or by two or more processors of the same kind or different kinds (for example, a plurality of FPGAs or a combination of a CPU and an FPGA). In addition, a plurality of processing units may be constituted by one processor.

Examples in which the plurality of processing units are constituted by one processor include a first configuration, as exemplified by computers such as a server and a client, in which a combination of one or more CPUs and software constitutes one processor and this processor functions as the plurality of processing units. The examples also include a second configuration, as exemplified by an SoC (System On Chip) or the like, in which a processor that implements functions of the entire system including the plurality of processing units on a single IC (Integrated Circuit) chip is used. As described above, the various processing units are configured using one or more of the various processors in terms of the hardware structure.

Further, the hardware structure of these various processors is, more specifically, electric circuitry in which circuit elements such as semiconductor elements are combined.

REFERENCE SIGNS LIST 1 similarity determining apparatus
2 three-dimensional imaging apparatus 3 image storage server
4 network
11 CPU
12 memory
13 storage
14 display unit
15 input unit
21 image acquiring unit
22 region dividing unit
23 findings classifying unit
24 feature quantity calculating unit
25 region similarity deriving unit
26 similarity deriving unit
27 search unit
28 display control unit
30 bronchus extracting unit
31 first dividing unit
32 second dividing unit
33 third dividing unit
34 fourth dividing unit
40L left lung region
40R right lung region
41 graph structure
50 multilayer neural network
51 input layer
52 output layer
61 search result
62 to 64 examination slice image
B1, B31 bronchi branch
DB case database
G1 tomographic image in an axial plane
G2 tomographic image in a coronal plane
G3 tomographic image in a sagital plane
L0 search result list
R1 to R4 similar case image
V0, V1 examination image

What is claimed is:

1. A similarity determining apparatus that determines a similarity between a first medical image including a lung and a second medical image including a lung, the similarity determining apparatus comprising a processor, the processor configured to:
extract a bronchus from a lung region included in a medical image acquired by imaging a subject including a lung;
identify a plurality of branch positions of the bronchus and divide, based on the branch positions, the lung region into a plurality of regions;
classify, by a multilayer neural network, each of pixels of the first medical image into at least one of findings, wherein the multilayer neural network is learned using a plurality of pieces of training data, and each piece of training data comprises a region of interest having a predetermined size for which a finding among the at least one of findings is known;
calculate, for each of the divided regions, first feature quantities for respective findings classified in the first medical image;
derive, for each of the divided regions, a region similarity between the first medical image and the second medical image, based on the first feature quantities for the respective findings calculated in the first medical image and second feature quantities for the respective findings calculated in advance in the second medical image; and
derive a similarity between the first medical image and the second medical image, based on the plurality of region similarities, and wherein the processor is configured to classify the findings to a background findings group or a lesion findings group,
wherein the processor is configured to divide the lung region into a region that is within a specific distance from a specific branch position among the plurality of branch positions and a region other than the region that is within the specific distance, wherein the region that is within the specific distance from the specific branch position is a spherical region that is centered at the specific branch position and the spherical region has a radius being equal to the specific distance.

2. The similarity determining apparatus according to claim 1,
wherein the processor is configured to divide the lung region into three regions with reference to a first bronchi branch and a third bronchi branch among the plurality of branch positions, the three regions being an upper region, a middle region, and a lower region.

3. The similarity determining apparatus according to claim 2,
wherein the processor is configured to divide the lung region into a region that is within a specific distance from a specific branch position among the plurality of branch positions and a region other than the region that is within the specific distance.

4. The similarity determining apparatus according to claim 1,
wherein the processor is configured to set a third bronchi branch as the specific branch position among the plurality of branch positions, and divide the lung region into a central region that is within the specific distance from the third bronchi branch and a region other than the central region.

5. The similarity determining apparatus according to claim 1,
wherein the processor is configured to divide the lung region into an outer region and an inner region.

6. The similarity determining apparatus according to claim 2,
wherein the processor is configured to divide the lung region into an outer region and an inner region.

7. The similarity determining apparatus according to claim 1,
wherein the processor is configured to divide the lung region into a dorsal region and a ventral region.

8. The similarity determining apparatus according to claim 2,
wherein the processor is configured to divide the lung region into a dorsal region and a ventral region.

9. A feature quantity deriving apparatus comprising a processor, the processor is configured to:
extract a bronchus from a lung region included in a medical image;
identify a plurality of branch positions of the bronchus and divide, based on the branch positions, the lung region into a plurality of regions;
classify, by a multilayer neural network, each of pixels of the medical image into at least one of findings, wherein the multilayer neural network is learned using a plurality of pieces of training data, and each piece of training data comprises a region of interest having a predetermined size for which a finding among the at least one of findings is known; and
calculate, for each of the divided regions, feature quantities for respective findings classified in the medical image, and wherein the processor is configured to classify the findings to a background findings group or a lesion findings group, wherein the processor is configured to divide the lung region into a region that is within a specific distance from a specific branch position among the plurality of branch positions and a region other than the region that is within the specific distance, wherein the region that is within the specific distance from the specific branch position is a spherical region that is centered at the specific branch position and the spherical region has a radius being equal to the specific distance.

10. The feature quantity deriving apparatus according to claim 9, wherein the second processor is configured to control to display the feature quantities on a display.

11. A similarity determining method for determining a similarity between a first medical image including a lung and a second medical image including a lung, the similarity determining method comprising:

extracting a bronchus from a lung region included in a medical image acquired by imaging a subject including a lung;

identifying a plurality of branch positions of the bronchus and dividing, based on the branch positions, the lung region into a plurality of regions;

dividing a lung region in the first medical image into a plurality of regions;

classifying, by a multilayer neural network, each of pixels of the first medical image into at least one of findings, wherein the multilayer neural network is learned using a plurality of pieces of training data, and each piece of training data comprises a region of interest having a predetermined size for which a finding among the at least one of findings is known;

calculating, for each of the divided regions, first feature quantities for respective findings classified in the first medical image;

deriving, for each of the divided regions, a region similarity between the first medical image and the second medical image, based on the first feature quantities for the respective findings calculated in the first medical image and second feature quantities for the respective findings calculated in advance in the second medical image;

deriving a similarity between the first medical image and the second medical image, based on the plurality of region similarities; and classifying the findings to a background findings group or a lesion findings group, wherein the lung region is divided into a region that is within a specific distance from a specific branch position among the plurality of branch positions and a region other than the region that is within the specific distance, wherein the region that is within the specific distance from the specific branch position is a spherical region that is centered at the specific branch position and the spherical region has a radius being equal to the specific distance.

12. A feature quantity deriving method comprising:

extracting a bronchus from a lung region included in a medical image acquired by imaging a subject including a lung;

identifying a plurality of branch positions of the bronchus and dividing, based on the branch positions, the lung region into a plurality of regions;

dividing a lung region in the medical image into a plurality of regions;

classifying, by a multilayer neural network, each of pixels of the medical image into at least one of findings, wherein the multilayer neural network is learned using a plurality of pieces of training data, and each piece of training data comprises a region of interest having a predetermined size for which a finding among the at least one of findings is known; and calculating, for each of the divided regions, feature quantities for respective findings classified in the medical image, wherein the lung region is divided into a region that is within a specific distance from a specific branch position among the plurality of branch positions and a region other than the region that is within the specific distance, wherein the region that is within the specific distance from the specific branch position is a spherical region that is centered at the specific branch position and the spherical region has a radius being equal to the specific distance.

13. A non-transitory computer readable recording medium storing a similarity determining program causing a computer to execute a similarity determining method according to claim 11.

14. A non-transitory computer readable recording medium storing a feature quantity deriving program causing a computer to execute a feature quantity deriving method according to claim 12.

* * * * *